(12) United States Patent
Denison et al.

(10) Patent No.: US 10,849,685 B2
(45) Date of Patent: Dec. 1, 2020

(54) PERI-VASCULAR TISSUE ACCESS CATHETER WITH LOCKING HANDLE

(71) Applicant: Ablative Solutions, Inc., San Jose, CA (US)

(72) Inventors: Andy Edward Denison, Temecula, CA (US); David R. Fischell, Fair Haven, NJ (US); Tim A. Fischell, Kalamazoo, MI (US); Darrin James Kent, Murrieta, CA (US); Nicole Haratani, San Jose, CA (US)

(73) Assignee: Ablative Solutions, Inc., San Jose, CA (US)

( * ) Notice: Subject to any disclaimer, the term of this patent is extended or adjusted under 35 U.S.C. 154(b) by 0 days.

(21) Appl. No.: 16/039,234

(22) Filed: Jul. 18, 2018

(65) Prior Publication Data

US 2020/0022751 A1   Jan. 23, 2020

(51) Int. Cl.
*A61B 18/14* (2006.01)
*A61B 90/00* (2016.01)
(Continued)

(52) U.S. Cl.
CPC .......... *A61B 18/1492* (2013.01); *A61B 18/06* (2013.01); *A61B 18/1477* (2013.01); *A61B 90/39* (2016.02); *A61B 2018/00011* (2013.01); *A61B 2018/00214* (2013.01); *A61B 2018/00351* (2013.01); *A61B 2018/00404* (2013.01); *A61B 2018/00434* (2013.01); *A61B 2018/00511* (2013.01); *A61B 2018/00517* (2013.01); *A61B 2018/00577* (2013.01);
(Continued)

(58) Field of Classification Search
CPC .......... A61M 2025/0681; A61M 2025/09125; A61M 2025/09116; A61M 25/0136; A61M 2025/1066; A61M 2025/0175
See application file for complete search history.

(56) References Cited

U.S. PATENT DOCUMENTS

| 4,578,061 A | 3/1986 | Lemelson |
| 4,798,595 A | 1/1989 | Anderson et al. |

(Continued)

FOREIGN PATENT DOCUMENTS

| CN | 1147964 | 4/1997 |
| CN | 1494399 | 5/2004 |

(Continued)

OTHER PUBLICATIONS

U.S. Appl. No. 15/940,178, filed Mar. 29, 2018, Fischell, et al.
(Continued)

*Primary Examiner* — Nathan R Price
*Assistant Examiner* — Melissa A Snyder
(74) *Attorney, Agent, or Firm* — Knobbe, Martens, Olson & Bear, LLP

(57) ABSTRACT

An intravascular catheter for peri-vascular and/or peri-urethral tissue ablation includes multiple penetrators advanced through supported guide tubes which expand around a central axis to engage the interior surface of the wall of the renal artery or other vessel of a human body allowing the injection an ablative fluid for ablating tissue, nerve sensing, nerve stimulation, or ablation by application of energy. The catheter can include a proximal handle for the advancement of guide tubes and penetrators.

18 Claims, 6 Drawing Sheets

(51) Int. Cl.
*A61B 18/06* (2006.01)
*A61B 18/00* (2006.01)
*A61M 25/06* (2006.01)
*A61M 25/00* (2006.01)
*A61B 18/04* (2006.01)

(52) U.S. Cl.
CPC ... *A61B 2018/046* (2013.01); *A61B 2018/143* (2013.01); *A61B 2018/1475* (2013.01); *A61B 2090/376* (2016.02); *A61M 25/0068* (2013.01); *A61M 25/0074* (2013.01); *A61M 25/0084* (2013.01); *A61M 25/0662* (2013.01)

(56) References Cited

U.S. PATENT DOCUMENTS

| | | |
|---|---|---|
| 5,304,141 A | 4/1994 | Johnson et al. |
| 5,354,279 A | 10/1994 | Hofling |
| 5,385,562 A | 1/1995 | Adams et al. |
| 5,405,376 A | 4/1995 | Mulier et al. |
| 5,419,777 A | 5/1995 | Hofling |
| 5,431,649 A | 7/1995 | Mulier et al. |
| 5,464,395 A | 11/1995 | Faxon et al. |
| 5,474,102 A | 12/1995 | Lopez |
| 5,551,426 A | 9/1996 | Hummel et al. |
| 5,588,960 A | 12/1996 | Edwards et al. |
| 5,667,488 A | 9/1997 | Lundquist et al. |
| 5,672,173 A | 9/1997 | Gough |
| 5,683,384 A | 11/1997 | Gough |
| 5,713,863 A | 2/1998 | Vigil et al. |
| 5,792,094 A | 8/1998 | Stevens et al. |
| 5,800,379 A | 9/1998 | Edwards |
| 5,855,576 A | 1/1999 | LeVeen et al. |
| 5,902,289 A | 5/1999 | Swartz et al. |
| 5,971,958 A | 10/1999 | Zhang |
| 5,980,516 A | 11/1999 | Mulier et al. |
| 6,056,744 A | 5/2000 | Edwards |
| 6,106,521 A | 8/2000 | Blewett et al. |
| 6,165,164 A | 12/2000 | Hill et al. |
| 6,190,353 B1 | 2/2001 | Makower et al. |
| 6,190,393 B1 | 2/2001 | Bevier et al. |
| 6,217,554 B1 | 4/2001 | Green |
| 6,221,049 B1 | 4/2001 | Selmon et al. |
| 6,231,597 B1 | 5/2001 | Deem et al. |
| 6,254,599 B1 | 7/2001 | Lesh et al. |
| 6,277,107 B1 | 8/2001 | Lurie et al. |
| 6,283,947 B1 | 9/2001 | Mirzaee |
| 6,283,951 B1 | 9/2001 | Flaherty et al. |
| 6,302,870 B1 | 10/2001 | Jacobsen et al. |
| 6,375,660 B1 | 4/2002 | Fischell et al. |
| 6,416,510 B1 | 7/2002 | Altman et al. |
| 6,432,092 B2 | 8/2002 | Miller |
| 6,478,778 B1 | 11/2002 | Jacobsen et al. |
| 6,514,248 B1 | 2/2003 | Eggers et al. |
| 6,547,803 B2 | 4/2003 | Seward et al. |
| 6,599,267 B1 | 7/2003 | Ray et al. |
| 6,652,517 B1 | 11/2003 | Hall et al. |
| 6,685,648 B2 | 2/2004 | Flaherty et al. |
| 6,692,466 B1 | 2/2004 | Chow et al. |
| 6,764,461 B2 | 7/2004 | Mickley et al. |
| 6,854,467 B2 | 2/2005 | Boekstegers |
| 6,855,124 B1 | 2/2005 | Gonzalez et al. |
| 6,905,480 B2 | 6/2005 | McGuckin et al. |
| 6,966,897 B2 | 11/2005 | Shimazaki |
| 6,978,174 B2 | 12/2005 | Gelfand et al. |
| 6,997,903 B2 | 2/2006 | Wijay et al. |
| 7,015,253 B2 | 3/2006 | Escandon et al. |
| 7,056,286 B2 | 6/2006 | Ravenscroft et al. |
| 7,087,040 B2 | 8/2006 | McGuckin, Jr. et al. |
| 7,094,202 B2 | 8/2006 | Nobis et al. |
| 7,162,303 B2 | 1/2007 | Levin et al. |
| 7,181,288 B1 | 2/2007 | Rezai et al. |
| 7,273,469 B1 | 9/2007 | Chan et al. |
| 7,472,705 B2 | 1/2009 | Baran |
| 7,617,005 B2 | 11/2009 | Demarais et al. |
| 7,621,945 B2 | 11/2009 | Lennox et al. |
| 7,647,115 B2 | 1/2010 | Levin et al. |
| 7,653,438 B2 | 1/2010 | Deem et al. |
| 7,666,163 B2 | 2/2010 | Seward et al. |
| 7,691,080 B2 | 4/2010 | Seward et al. |
| 7,691,086 B2 | 4/2010 | Tkebuchava |
| 7,717,899 B2 | 5/2010 | Bowe et al. |
| 7,717,948 B2 | 5/2010 | Demarais et al. |
| 7,744,584 B2 | 6/2010 | Seward et al. |
| 7,756,583 B2 | 7/2010 | Demarais et al. |
| 7,794,444 B2 | 9/2010 | Lesh et al. |
| 7,850,656 B2 | 12/2010 | McKay et al. |
| 7,862,563 B1 | 1/2011 | Cosman et al. |
| 7,873,417 B2 | 1/2011 | Demarais et al. |
| 7,881,807 B2 | 2/2011 | Schaer |
| 7,942,854 B1 | 5/2011 | Von Oepen et al. |
| 8,000,764 B2 | 8/2011 | Rashidi |
| 8,088,127 B2 | 1/2012 | Mayse et al. |
| 8,100,883 B1 | 1/2012 | Johnson |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,758 B2 | 4/2012 | Chan et al. |
| 8,152,804 B2 | 4/2012 | Elmouelhi et al. |
| 8,175,711 B2 | 5/2012 | Demarais et al. |
| 8,396,548 B2 | 3/2013 | Perry et al. |
| 8,399,443 B2 | 3/2013 | Seward et al. |
| 8,465,451 B2 | 6/2013 | McRae et al. |
| 8,465,752 B2 | 6/2013 | Seward |
| 8,663,190 B2 | 3/2014 | Fischell et al. |
| 8,684,998 B2 | 4/2014 | Demarais et al. |
| 8,708,995 B2 | 4/2014 | Seward et al. |
| 8,740,849 B1 | 6/2014 | Fischell et al. |
| 8,771,252 B2 | 7/2014 | Gelfand et al. |
| 8,852,163 B2 | 10/2014 | Deem et al. |
| 8,880,186 B2 | 11/2014 | Levin et al. |
| 8,934,978 B2 | 1/2015 | Deem et al. |
| 8,948,865 B2 | 2/2015 | Zarins et al. |
| 8,975,233 B2 | 3/2015 | Stein et al. |
| 8,979,801 B2 | 3/2015 | Lamson et al. |
| 8,983,595 B2 | 3/2015 | Levin et al. |
| 9,011,879 B2 | 4/2015 | Seward |
| 9,056,185 B2 | 6/2015 | Fischell et al. |
| 9,125,661 B2 | 9/2015 | Deem et al. |
| 9,131,978 B2 | 9/2015 | Zarins et al. |
| 9,131,983 B2 | 9/2015 | Fischell et al. |
| 9,138,281 B2 | 9/2015 | Zarins et al. |
| 9,179,962 B2 | 11/2015 | Fischell et al. |
| 9,192,715 B2 | 11/2015 | Gelfand et al. |
| 9,199,065 B2 | 12/2015 | Seward |
| 9,237,925 B2 | 1/2016 | Fischell et al. |
| 9,254,360 B2 | 2/2016 | Fischell et al. |
| 9,265,558 B2 | 2/2016 | Zarins et al. |
| 9,278,196 B2 | 3/2016 | Fischell et al. |
| 9,289,255 B2 | 3/2016 | Deem et al. |
| 9,301,795 B2 | 4/2016 | Fischell et al. |
| 9,308,044 B2 | 4/2016 | Zarins et al. |
| 9,314,630 B2 | 4/2016 | Levin et al. |
| 9,320,561 B2 | 4/2016 | Zarins et al. |
| 9,320,850 B2 | 4/2016 | Fischell et al. |
| 9,326,817 B2 | 5/2016 | Zarins et al. |
| 9,439,726 B2 | 9/2016 | Zarins et al. |
| 9,456,869 B2 | 10/2016 | Zarins et al. |
| 9,474,563 B2 | 10/2016 | Zarins et al. |
| 9,486,270 B2 | 11/2016 | Zarins et al. |
| 9,526,827 B2 | 12/2016 | Fischell et al. |
| 9,539,047 B2 | 1/2017 | Fischell et al. |
| 9,554,849 B2 | 1/2017 | Fischell et al. |
| 9,629,675 B2 | 4/2017 | Kleshinski et al. |
| 9,636,174 B2 | 5/2017 | Zarins et al. |
| 9,675,413 B2 | 6/2017 | Deem et al. |
| 9,743,983 B2 | 8/2017 | Levin et al. |
| 9,757,192 B2 | 9/2017 | Levin et al. |
| 9,789,276 B2 | 10/2017 | Seward et al. |
| 9,795,441 B2 | 10/2017 | Fischell et al. |

(56) References Cited

U.S. PATENT DOCUMENTS

| | | |
|---|---|---|
| 9,814,873 B2 | 11/2017 | Zarins et al. |
| 9,895,195 B2 | 2/2018 | Zarins et al. |
| 9,907,611 B2 | 3/2018 | Levin et al. |
| 9,931,046 B2 | 4/2018 | Fischell et al. |
| 9,949,652 B2 | 4/2018 | Fischell et al. |
| 9,993,278 B2 | 6/2018 | Rioux et al. |
| 10,022,059 B2 | 7/2018 | Fischell et al. |
| 10,118,004 B2 | 11/2018 | Fischell et al. |
| 10,172,663 B2 | 1/2019 | Fischell et al. |
| 10,226,278 B2 | 3/2019 | Fischell et al. |
| 10,350,392 B2 | 7/2019 | Fischell et al. |
| 10,405,912 B2 | 9/2019 | Fischell et al. |
| 10,420,481 B2 | 9/2019 | Fischell et al. |
| 10,485,951 B2 | 11/2019 | Fischell et al. |
| 10,517,666 B2 | 12/2019 | Fischell et al. |
| 10,576,246 B2 | 3/2020 | Fischell et al. |
| 2001/0037065 A1 | 11/2001 | Graf et al. |
| 2002/0010439 A1 | 1/2002 | Miller |
| 2002/0052577 A1 | 5/2002 | Shimazaki et al. |
| 2002/0082584 A1 | 6/2002 | Rosenman et al. |
| 2002/0120238 A1 | 8/2002 | McGuckin et al. |
| 2002/0151866 A1 | 10/2002 | Lundkvist et al. |
| 2002/0177846 A1 | 11/2002 | Mulier et al. |
| 2002/0183738 A1 | 12/2002 | Chee et al. |
| 2003/0032929 A1 | 2/2003 | McGuckin, Jr. |
| 2003/0171723 A1 | 9/2003 | Ponzi |
| 2004/0064098 A1 | 4/2004 | Cuschieri et al. |
| 2004/0133154 A1 | 7/2004 | Flaherty et al. |
| 2004/0147902 A1 | 7/2004 | McGuckin, Jr. et al. |
| 2005/0070885 A1 | 3/2005 | Nobis et al. |
| 2005/0096647 A1 | 5/2005 | Steinke et al. |
| 2005/0187546 A1 | 8/2005 | Bek et al. |
| 2005/0234437 A1 | 10/2005 | Baxter et al. |
| 2005/0245923 A1 | 11/2005 | Christopherson et al. |
| 2005/0288730 A1 | 12/2005 | Deem et al. |
| 2006/0064065 A1 | 3/2006 | Russo |
| 2006/0173440 A1 | 8/2006 | Lamson et al. |
| 2006/0189940 A1 | 8/2006 | Kirsch |
| 2006/0224118 A1 | 10/2006 | Morris et al. |
| 2006/0271111 A1 | 11/2006 | Demarais et al. |
| 2006/0271135 A1 | 11/2006 | Minar et al. |
| 2007/0005018 A1 | 1/2007 | Tekbuchava |
| 2007/0060812 A1 | 3/2007 | Harel et al. |
| 2007/0083239 A1 | 4/2007 | Demarias et al. |
| 2007/0129720 A1 | 6/2007 | Demarais et al. |
| 2007/0129760 A1 | 6/2007 | Demarais et al. |
| 2007/0173899 A1 | 7/2007 | Levin et al. |
| 2007/0203549 A1 | 8/2007 | Demarais et al. |
| 2007/0244479 A1 | 10/2007 | Beatty et al. |
| 2007/0270751 A1 | 11/2007 | Stangenes |
| 2007/0270757 A1 | 11/2007 | Willis et al. |
| 2008/0045890 A1 | 2/2008 | Seward et al. |
| 2008/0051756 A1 | 2/2008 | Makower et al. |
| 2008/0188812 A1 | 8/2008 | Valaie |
| 2008/0213331 A1 | 9/2008 | Gelfand et al. |
| 2008/0300454 A1 | 12/2008 | Goto |
| 2009/0018526 A1 | 1/2009 | Power |
| 2009/0018638 A1 | 1/2009 | Shirley et al. |
| 2009/0036948 A1 | 2/2009 | Levin et al. |
| 2009/0076500 A1 | 3/2009 | Azure |
| 2009/0312617 A1 | 12/2009 | Creed et al. |
| 2010/0076545 A1 | 3/2010 | Kleshinski et al. |
| 2010/0114087 A1 | 5/2010 | Edwards |
| 2010/0137860 A1 | 6/2010 | Demarais et al. |
| 2010/0137952 A1 | 6/2010 | Demarais et al. |
| 2010/0179416 A1 | 7/2010 | Hoey et al. |
| 2010/0191112 A1 | 7/2010 | Demarais et al. |
| 2010/0222851 A1 | 9/2010 | Deem et al. |
| 2010/0268307 A1 | 10/2010 | Demarais et al. |
| 2010/0305546 A1 | 12/2010 | Seward et al. |
| 2010/0324446 A1* | 12/2010 | Pendleton .............. A61B 10/06 600/565 |
| 2011/0009848 A1 | 1/2011 | Woodard et al. |
| 2011/0104060 A1 | 5/2011 | Seward |
| 2011/0104061 A1 | 5/2011 | Seward |
| 2011/0112400 A1 | 5/2011 | Emery et al. |
| 2011/0146674 A1 | 6/2011 | Roschak |
| 2011/0172593 A1 | 7/2011 | Lyyikainen et al. |
| 2011/0182912 A1 | 7/2011 | Evans et al. |
| 2011/0184337 A1 | 7/2011 | Evans et al. |
| 2011/0195971 A1 | 8/2011 | Cincotta |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257564 A1 | 10/2011 | Demarais et al. |
| 2011/0257622 A1 | 10/2011 | Salahieh et al. |
| 2011/0295354 A1* | 12/2011 | Bueche ................ A61F 2/966 623/1.11 |
| 2012/0010524 A1 | 1/2012 | Fojtik et al. |
| 2012/0053604 A1 | 3/2012 | DiCaprio |
| 2012/0071832 A1 | 3/2012 | Bunch |
| 2012/0083877 A1 | 4/2012 | Nguyen et al. |
| 2012/0101490 A1 | 4/2012 | Smith |
| 2012/0108517 A1 | 5/2012 | Evans et al. |
| 2012/0116438 A1 | 5/2012 | Salahieh et al. |
| 2012/0130269 A1 | 5/2012 | Rea |
| 2012/0130289 A1 | 5/2012 | Demarais et al. |
| 2012/0130345 A1 | 5/2012 | Levin et al. |
| 2012/0143181 A1 | 6/2012 | Demarais et al. |
| 2012/0197198 A1 | 8/2012 | Demarais et al. |
| 2012/0197252 A1 | 8/2012 | Deem et al. |
| 2012/0253186 A1 | 10/2012 | Simpson et al. |
| 2012/0253192 A1 | 10/2012 | Cressman |
| 2012/0271277 A1 | 10/2012 | Fischell et al. |
| 2012/0271301 A1 | 10/2012 | Fischell et al. |
| 2012/0296329 A1 | 11/2012 | Ng |
| 2013/0053792 A1 | 2/2013 | Fischell et al. |
| 2013/0053821 A1 | 2/2013 | Fischell et al. |
| 2013/0053822 A1 | 2/2013 | Fischell et al. |
| 2013/0090637 A1 | 4/2013 | Sliwa |
| 2013/0103026 A1 | 4/2013 | Kleshinski et al. |
| 2013/0131743 A1 | 5/2013 | Yamasaki et al. |
| 2013/0138082 A1 | 5/2013 | Salahieh et al. |
| 2013/0144251 A1 | 6/2013 | Sobotka |
| 2013/0178910 A1 | 7/2013 | Azamian et al. |
| 2013/0274614 A1 | 10/2013 | Shimada et al. |
| 2013/0274673 A1 | 10/2013 | Fischell et al. |
| 2013/0274674 A1 | 10/2013 | Fischell et al. |
| 2013/0287698 A1 | 10/2013 | Seward |
| 2014/0024959 A1 | 1/2014 | Sobotka |
| 2014/0046298 A1 | 2/2014 | Fischell et al. |
| 2014/0121641 A1 | 5/2014 | Fischell et al. |
| 2014/0121644 A1 | 5/2014 | Fischell et al. |
| 2014/0236103 A1 | 8/2014 | Fischell et al. |
| 2014/0316351 A1 | 10/2014 | Fischell et al. |
| 2014/0358079 A1 | 12/2014 | Fischell et al. |
| 2014/0378906 A1 | 12/2014 | Fischell et al. |
| 2015/0005719 A1 | 1/2015 | Fischell et al. |
| 2015/0119674 A1* | 4/2015 | Fischell ............. A61B 5/04001 600/381 |
| 2015/0119875 A1 | 4/2015 | Fischell et al. |
| 2015/0132409 A1 | 5/2015 | Stein et al. |
| 2015/0202220 A1 | 7/2015 | Stein et al. |
| 2015/0224289 A1 | 8/2015 | Seward |
| 2015/0245863 A1 | 9/2015 | Fischell et al. |
| 2015/0335384 A1 | 11/2015 | Fischell et al. |
| 2015/0343156 A1 | 12/2015 | Fischell et al. |
| 2016/0045257 A1 | 2/2016 | Fischell et al. |
| 2016/0058489 A1 | 3/2016 | Fischell et al. |
| 2016/0120587 A1 | 5/2016 | Fischell et al. |
| 2016/0235464 A1 | 8/2016 | Fischell et al. |
| 2016/0242661 A1 | 8/2016 | Fischell et al. |
| 2016/0279384 A1 | 9/2016 | Zarins et al. |
| 2016/0354137 A1 | 12/2016 | Fischell et al. |
| 2017/0119408 A1 | 5/2017 | Ma |
| 2017/0119974 A1 | 5/2017 | Racz |
| 2017/0304594 A1 | 10/2017 | Fischell et al. |
| 2017/0326363 A1 | 11/2017 | Deem et al. |
| 2017/0332926 A1 | 11/2017 | Fischell et al. |
| 2018/0043107 A1 | 2/2018 | Hooven et al. |
| 2018/0071019 A1 | 3/2018 | Fischell et al. |
| 2018/0193596 A1 | 7/2018 | Fischell et al. |
| 2018/0279894 A1 | 10/2018 | Fischell et al. |
| 2019/0008580 A1 | 1/2019 | Fischell et al. |

(56) References Cited

U.S. PATENT DOCUMENTS

| | | |
|---|---|---|
| 2019/0015002 A1 | 1/2019 | Fischell et al. |
| 2019/0076186 A1 | 3/2019 | Fischell et al. |
| 2019/0076187 A1 | 3/2019 | Fischell et al. |
| 2019/0076188 A1 | 3/2019 | Fischell et al. |
| 2019/0117936 A9 | 4/2019 | Fischell et al. |
| 2019/0167918 A1 | 6/2019 | Fischell et al. |
| 2019/0201070 A1 | 7/2019 | Fischell et al. |
| 2019/0269435 A1 | 9/2019 | Fischell et al. |
| 2020/0022751 A1 | 1/2020 | Fischell et al. |
| 2020/0061348 A1 | 2/2020 | Fischell et al. |

FOREIGN PATENT DOCUMENTS

| | | |
|---|---|---|
| CN | 1927130 | 3/2007 |
| EP | 0834288 | 4/1998 |
| EP | 0876805 | 8/2006 |
| JP | H06-277294 | 10/1994 |
| JP | H07509389 | 10/1995 |
| JP | H0889582 | 4/1996 |
| JP | 2001527428 | 12/2001 |
| JP | 2002510229 | 4/2002 |
| JP | 2002542901 | 12/2002 |
| JP | 2003-510126 | 3/2003 |
| JP | 2004-505689 | 2/2004 |
| JP | 2004516042 | 6/2004 |
| JP | 2005-40599 | 2/2005 |
| JP | 2008506500 | 3/2008 |
| JP | 09509865 | 3/2009 |
| JP | 2013-517847 | 5/2013 |
| WO | WO94/04220 | 3/1994 |
| WO | WO 95/13752 | 5/1995 |
| WO | WO 2004/030740 | 4/2004 |
| WO | WO 2007/121143 | 10/2007 |
| WO | WO 2009/137819 | 11/2009 |
| WO | WO 2009/141727 | 11/2009 |
| WO | WO 2010/124120 | 10/2010 |
| WO | WO 2011/094367 | 8/2011 |
| WO | WO 2012/145300 | 10/2012 |
| WO | WO 2012/145304 | 10/2012 |
| WO | WO 2013/028781 | 2/2013 |
| WO | WO 2013/112844 | 8/2013 |
| WO | WO 2013/159066 | 10/2013 |
| WO | WO 2014/070558 | 5/2014 |
| WO | WO 2015/061614 | 4/2015 |
| WO | WO 2015/168314 | 11/2015 |
| WO | WO 2019/195625 | 10/2019 |

OTHER PUBLICATIONS

U.S. Appl. No. 15/947,460, filed Apr. 6, 2018, Fischell, et al.
U.S. Appl. No. 15/947,618, filed Apr. 6, 2018, Fischell, et al.
U.S. Appl. No. 15/947,619, filed Apr. 6, 2018, Fischell, et al.
U.S. Appl. No. 15/947,626, filed Apr. 6, 2018, Fischell, et al.
U.S. Appl. No. 16/034,854, filed Jul. 13, 2018, Fischell, et al.
U.S. Appl. No. 16/039,234, filed Jul. 18, 2018, Fischell, et al.
Angelini et al., Retractable-Needle Catheters: An Updated on Local Drug Delivery in Coronary Interventions, Texas Heart Institute Journal, 2008, p. 419-424.
Bello-Reuss et al., Effects of Acute Unilateral Renal Denervation in the Rat, J. of Clinical Investigation, vol. 56, Jul. 1975, p. 208-217.
Berne, Hemodynamics and Sodium Excretion of Denervated Kidney in Anesthetized and Unanesthetized Dog, Am. J. of Physiology, vol. 171, No. 1, Oct. 1952, p. 148-158.
Chinushi et al., "Blood Pressure and Autonomic Responses to Electrical Stimulation of the Renal Arterial Nerves Before and After Ablation of the Renal Artery", Hypertension, 2013, vol. 61, p. 450-456.
Dave, R.M., "The ClearWay™ RX Local Therapeutic Infusion Catheter", CathLab Digest, May 2010, vol. 18, No. 5, p. 1-6.
Demas et al., Novel method for localized, functional sympathetic nervous system denervation of peripheral tissue using guanethidine (Journal of Neuroscience Methods 112, 2001), p. 21-28.
Dorward et al., "Reflex Responses to Baroreceptor, Chemoreceptor and Nociceptor Inputs in Single Renal Sympathetic Neurons in the Rabbit and the Effects of Anaesthesia on Them", Journal of the Autonomic Nervous System, 1987, vol. 18, p. 39-54.
F Mahoud, C Ukena, RE Schmieder. Ambulatory Blood Pressure Changes After Renal Sympathetic Denervation in Patients With Resistant Hypertension. Jul. 8, 2013 AHA Circulation 2013;128:132-140.
Gado et al., "Intra-articular guanethidine injection for resistant shoulder pain: a preliminary double blind study of a novel approach" Annals of the Rheumatic Disease, 1996, p. 199-201.
Habara et al., "Novel Use of a Local Drug Delivery Catheter for Coronary Perforation", Journal of Invasive Cardiology, Jan. 2011, vol. 23, No. 1, p. 1-8.
Hamza et al., "Substantial Reduction in Single Sympathetic Nerve Firing After Renal Denervation in Patients With Resistant Hypertension", Nov. 19, 2012, p. 856-864.
Hsu et al., "The Use of Intravenous Guanethidine Block in the Management of Reflex Sympathic Dystrophy Syndrome of the Hand." Second Congress of the Hong Kong Orthopaedic Association, Nov. 1982, p. 93-105.
Hering et al., "Substantial Reduction in Single Sympathetic Nerve Firing After Renal Denervation in Patients With Resistant Hypertension", Nov. 19, 2012 in 15 pages.
Klein et al. "Functional reinnervation and development of supersensitivity to NE after renal denervation in rats" American Physiological Society, 1980, p. 353-358.
Klein et al., Effect of Renal Denervation on Arterial Pressure and Renal Norepinephrine Concentration in Wistar-Kyota and Spontaneously Hypersensitive Rats, Can. J. Physiology and Pharmacology, vol. 58, 1980, p. 1384-1388.
Markovic, B., et al., "Embolization With Absolute Ethanol Injection of Insufficiently Ligated Renal Artery After Open Nephrectomy"; Diagnostic and Interventional Radiology, Mar. 2011; vol. 17, Issue 1, p. 88-91.
"Multi-prong Infusion Needle Case Study", from the web site of peridot™ Precision Manufacturing, http://www.peridotcorp.com/casestudy.aspx, Copyright 2012, in 8 pages.
Nanni et al., Control of Hypertension by Ethanol Renal Ablation (Radiology 148:51-54, Jul. 1983), p. 52-54.
National Institute for Health and Care Excellence. Hypertension in adults: diagnosis and management. Aug. 24, 2011, NICE, CG127.
Owens et al., Percutaneous Peri-Adventitial Guanethidine Delivery Induces Renal Artery Sympathectomy: Preclinical Experience and Implication for Refractory Hypertension (Journal of Vascular Surgery 53:17S), p. 87S, Jun. 2011.
Roytta et al., Taxol-induced neuropathy: short-term effects of local injection (Journal of Neurocytology 13, 1984), p. 685-701.
S.J .Doletskiy et al. "Vysokochastotnaj Elektrotekhnika", M., 7-10 "Meditsina", 1980, p. 48-50, fig. 18-19.
Trostel et al., Do renal nerves chronically influence renal function and arterial pressure in spinal rats? (The American Physiological Society 1992), p. 1265-1270.
Verloop et al., Eligibility for percutaneous renal denervation: the importance of a systematic screening, Journal of Hypertension, 2013, p. 1-7.
Vink et al. Limited destruction of renal nerves after catheter-based renal denervation: results of a human case study, Nephrol Dial Transplant, 2014, p. 1-3.
YA Ashram, NH Abdel Wahab, IH Diab, Non-dipping pattern of nocturnal blood pressure in obstructive sleep apnea syndrom: Possible role of oxidative stress and endothelin-1 precursor. Feb. 14, 2013, Alexandria Journal of Medicine, 49, 153-161.
Zafonte et al., "Phenol and Alcohol Blocks for the Treatment of Spasticity", Physical medicine and rehabilitation clinics of North America, Nov. 2001, p. 817-832.
U.S. Appl. No. 16/238,780, filed Jan. 3, 2019, Fischell, et al.
U.S. Appl. No. 16/296,688, filed Mar. 8, 2019, Fischell, et al.
International Search Report and Written Opinion in PCT/US19/040849 dated Sep. 24, 2012 in 16 pages.
U.S. Appl. No. 16/561,599, filed Sep. 5, 2019, Fischell, et al.
U.S. Appl. No. 16/577,327, filed Sep. 20, 2019, Fischell, et al.
U.S. Appl. No. 16/689,604, filed Nov. 20, 2019, Fischell, et al.

(56) References Cited

OTHER PUBLICATIONS

U.S. Appl. No. 16/717,286, filed Dec. 17, 2019, Fischell, et al.

* cited by examiner

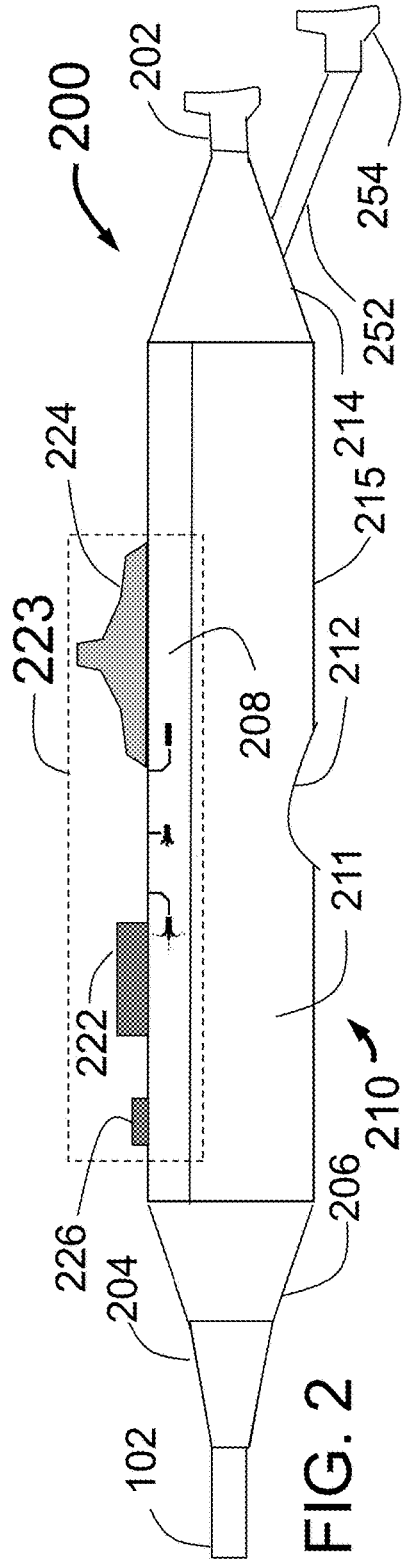
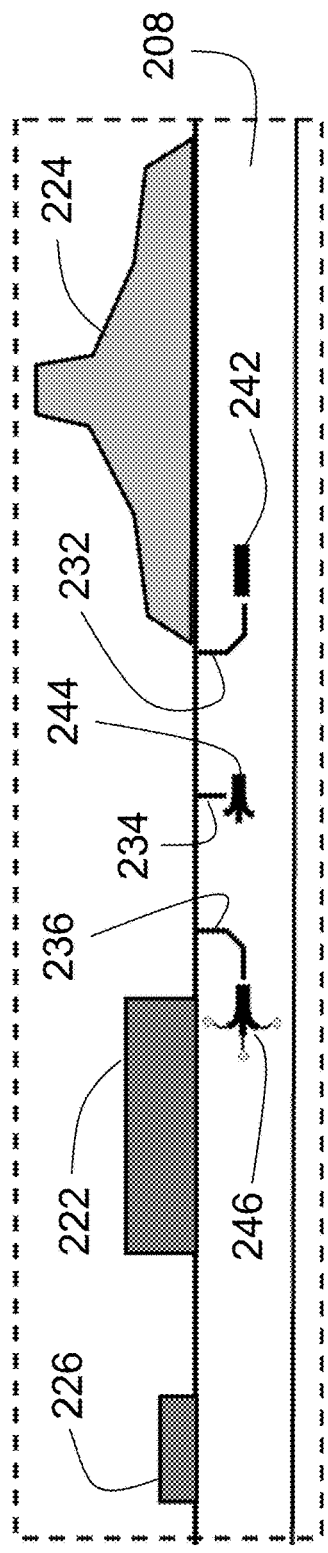
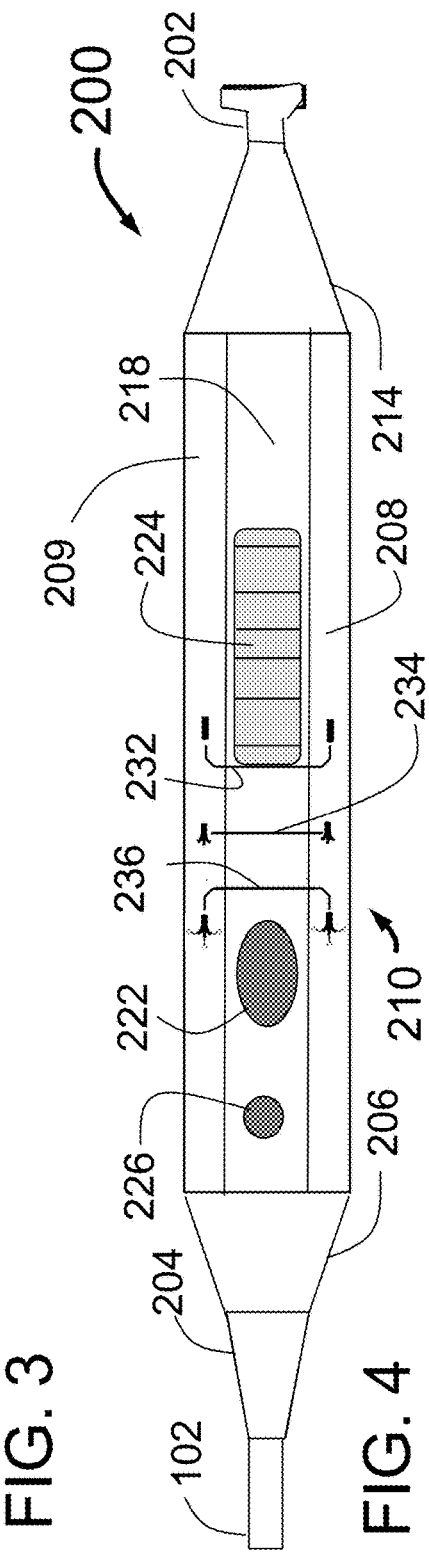

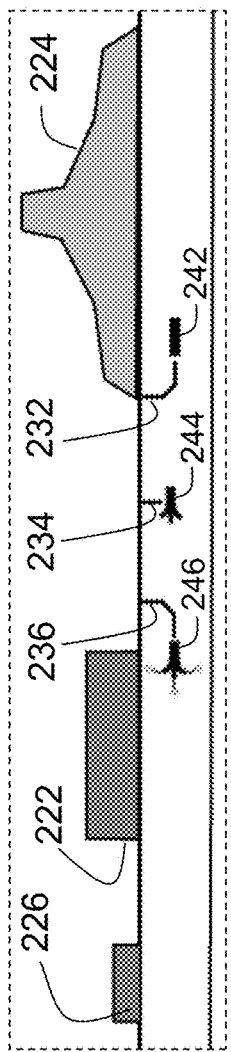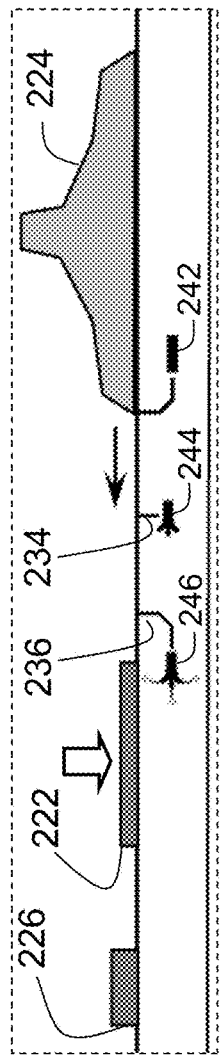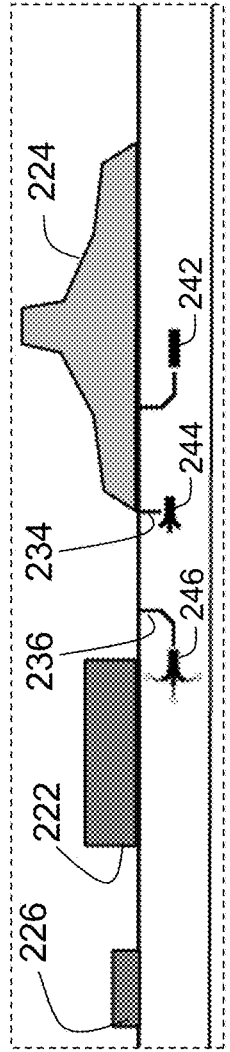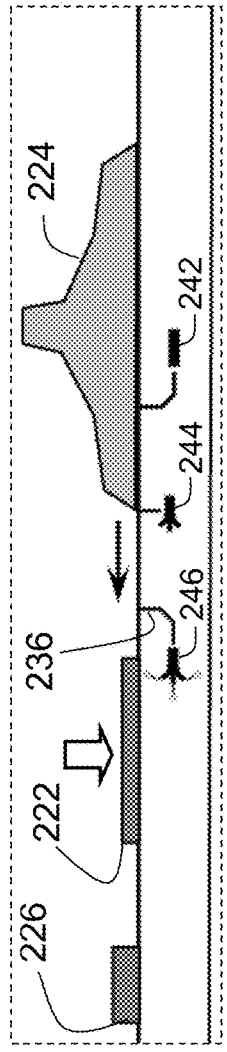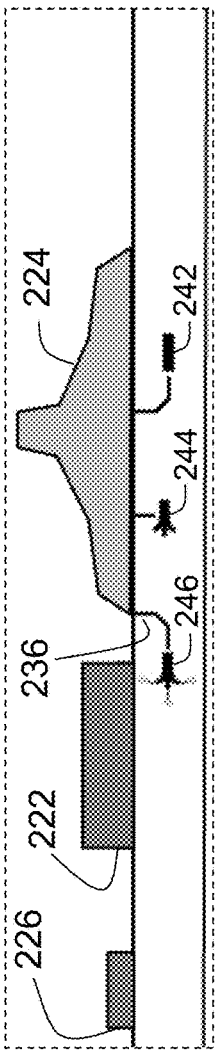

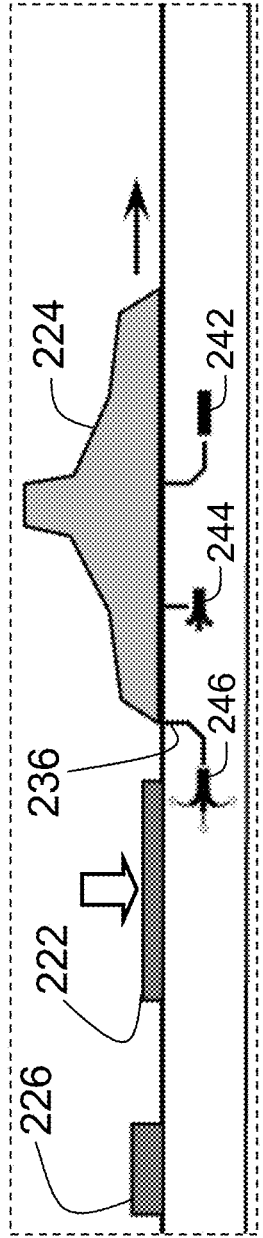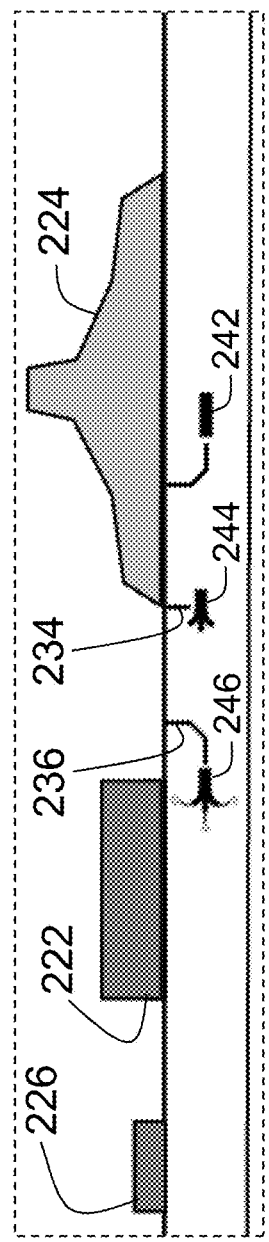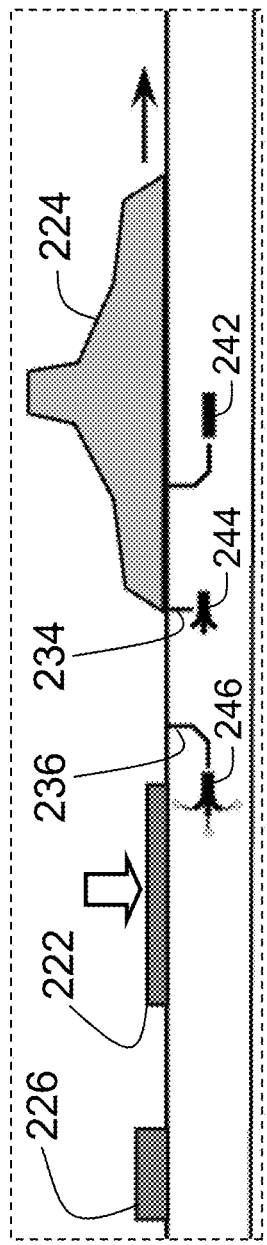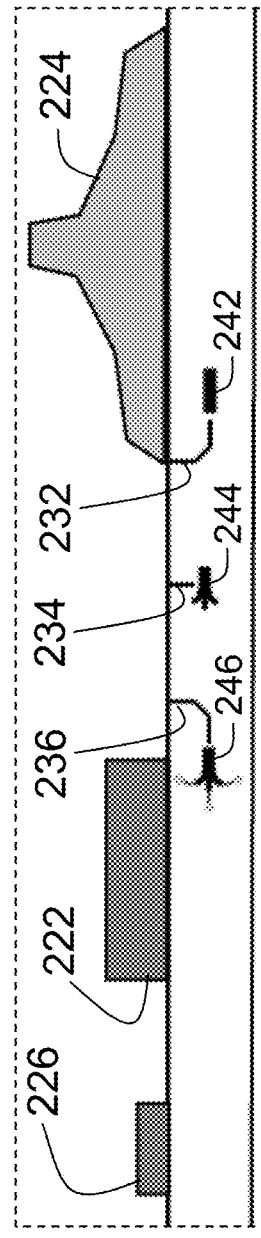

PERI-VASCULAR TISSUE ACCESS CATHETER WITH LOCKING HANDLE

FIELD

Some aspects of the invention are applicable to the field of devices to advance a needle-like structure for sensing nerve activity, tissue ablation or injection a fluid into a volume tissue outside of the inside wall of a target vessel of a human body. Applications include the treatment of hypertension, congestive heart failure, BPH and prostate cancer, prevention of restenosis after PCI and other disorders.

BACKGROUND

Fischell et al. in U.S. Pat. No. 9,056,185 describes an intravascular fluid injection catheter with a proximal handle having a gap between the two components of the handle and adjustment tools configured to adjust the gap. The gap can be used to limit the penetration depth of an injector tube with a distal needle beyond a guide tube that expands outward against the wall of a target vessel. This handle is workable but can lack a locking mechanism to prevent motion of the guide tubes or injector tubes. U.S. Pat. No. 9,056,185 is incorporated by reference in its entirety.

In U.S. Pat. Nos. 9,179,962, 9,254,360, 9,301,795, 9,320,850, 9,526,827, 9,539,047, and 9,554,849, which are incorporated by reference in their entireties, Fischell et al. show in FIG. 11, an improved handle with separate unlock mechanisms for the motion of the guide tubes and injector tubes with distal needles. A similar handle is shown by Fischell et al. in U.S. Pat. Nos. 9,931,046 and 9,949,652, incorporated by reference in their entireties, can be used to advance electrodes into and beyond the inside wall of a target vessel for nerve sensing, electrical stimulation and energy based tissue ablation.

Both sets of patents mentioned above use needle guiding elements in the form of guide tubes to support the advancement and penetration through the inside wall of a target vessel of needles/wires with sharpened distal ends. Such a structure can be important in some cases to allow use of small diameter needles/wires that may not cause blood loss when retracted for use in a blood vessel.

Throughout this specification any of the terms fluid or solution will be used interchangeably to include a liquid or a gaseous substance delivered into a volume of tissue in a human body with the intention of medicating, damaging, killing or ablating nerves or tissue within that volume of tissue.

Also throughout this specification, the term inside wall or interior surface applied to a blood vessel, vessel wall, artery or arterial wall mean the same thing which is the inside surface of the vessel wall inside of which is the vessel lumen. Also the term injection egress is defined as the distal opening in a needle from which a fluid being injected will emerge. With respect to the injection needle, either injection egress or distal opening may be used here interchangeably.

The terminology "deep to" a structure is defined as beyond or outside of the structure so that "deep to the inside wall of a target vessel" refers to a volume of tissue outside of the or inside surface of the vessel.

SUMMARY

The use of guide tubes as needle guiding elements of the catheters, such as the Peri-vascular Tissue Ablation Catheters (PTAC) of U.S. Pat. Nos. 9,056,185, 9,179,962, 9,254,360, 9,301,795, 9,320,850, 9,526,827, 9,539,047, and 9,554,849 can be utilized or modified for use with systems and methods as disclosed herein. Such guiding elements can be important in some cases for the support of small diameter needles to access the volume of tissue deep to the inside wall of a target vessel.

Some embodiments of handle features as disclosed herein can also be used or modified for use with, for example, the Sympathetic Nerve Sensing Catheter (SNSC) and Perivascular Nerve Sensing and Ablation Catheter (PNASC) embodiments described by Fischell et al. in U.S. Pat. Nos. 9,931,046 and 9,949,652 which include a guide tube/needle structure similar to for placing needles and/or electrodes deep to the inside wall of a target vessel.

Although not included in any of the above applications, a prototype handle using rings with a pin and slot mechanism was contemplated. While such handles can be used in some embodiments, they can in some cases be hard to use and requires hard to see visual verification of the pin location to see where the guide tubes or injector tubes are positioned.

Some embodiments of a catheter can include an improved handle that greatly simplifies the operation of the catheter allowing a single slider on the handle to sequentially advance and then retract the guide tubes and needles (or electrodes or other peripheral effectors) from an a pre-deployment state to where the guide tubes are deployed to where the needles are extended beyond the distal ends of the guide tubes into the desired volume of tissue and then back. A single unlock mechanism that may be in the form of a button or other control, can ensure that the system will under normal operation relock itself after each step.

The handle itself may have one or more additional physical features. These can include any number of:

An ergonomic shape with a finger detent to help properly position the user's hand for handle operation.

Marker lines or other indicia to easily verify the position of the guide tubes and needles/electrodes associated with the position of the slider, and Icons viewable on the handle surface to further verify the position of the guide tubes and needles/electrodes associated with the position of the slider.

An optional special fast retraction mode where using 2 hands, the needles and then guide tubes may be completely retracted in a single motion of the slider.

The addition of an unlock override to relock the device if it is unlocked in error.

As with the other handles referenced in the Fischell et al. patents, some embodiments of the present invention can include a fluid injection port and one or more flushing ports to flush air out of catheter lumens by the injection of saline. As described in U.S. Pat. No. 9,320,850, a handle may use a non-standard connector on the injection port to prevent accidental injection of the injectable fluid into a flushing port.

Throughout this specification the term injector tube with distal injection needle can be used to specify a tube with a sharpened distal end that penetrates into tissue and is used to inject a fluid into that tissue. Such a structure could also be called a hypodermic needle, an injection needle or simply a needle. In addition, the terms element and structure may be used interchangeably within the scope of this application. The term Luer fitting may be used throughout this application to mean a tapered Luer fitting without a screw cap or a Luer Lock fitting that has a screw cap.

These and other features and advantages of embodiments of the invention will become obvious to a person of ordinary skill in this art upon reading of the detailed description including the associated drawings and the claims.

In some embodiments, a catheter for fluid delivery to a volume of tissue in outside of the inside wall of a target lumen, e.g., vessel in a human body is provided. In some embodiments, the catheter can include a catheter body having a central axis extending in a longitudinal direction. The catheter can include a distal portion including at least one guide tube having a distal end, at least one guide tube expandable between a first position within the catheter body and a second position inclined away from the catheter body with the distal end in proximity to the inside wall of the target vessel. In some embodiments, the catheter can include at least one sharpened needle having an injection lumen with distal injection egress, a portion of the at least one injector tube located coaxially inside of the at least one guide tube. In some embodiments, the catheter can include a proximal handle having a top surface, two side surfaces and a bottom surface adapted to advance and retract the guide tubes and needles. In some embodiments, the handle can include an unlock mechanism having a locked state and an unlocked state. In some embodiments, the handle can include a movement mechanism configured to allow the relative longitudinal movement of the at least one guide tube with respect to the catheter body and the at least one needle with respect to the at least one guide tube, the movement subject to the unlock mechanism being in the unlocked state, and movement is prevented when the unlock mechanism is not in the unlocked state.

In some embodiments, the catheter can include three guide tubes and three sharpened needles. In some embodiments, the at least one needle is hollow and includes fluid egress near the distal end of the needle and the catheter can include an injection lumen in fluid communication with the fluid egress of the at least one needle. In some embodiments, the at least one needle has a distal end that forms an electrode. In some embodiments, the catheter body further including a wire that runs the length of the catheter to conduct electrical signals between the at least one electrode and a connector near the proximal end of the catheter. In some embodiments, the connector is adapted to connect the wire to external equipment. In some embodiments, the external equipment includes electronic systems selected from the group of: sensors configured to measure electrical signals, sensors to measure electrical signals sensed by the electrodes of the at least one needle, a signal generator configured to provide electrical stimulation signals to the electrodes of the at least one needle, or an energy delivery effector to provide energy based ablation through the electrodes of the at least on needle. In some embodiments, the proximal handle includes at least one marker line associated with the position of the movement mechanism denoting the catheter state selected from the group of: the position of the movement mechanism where the at least one guide tube and at least one injector tubes are both retracted, the position of the movement mechanism where the at least one guide tube is advanced but the at least one injector tube is retracted, or the position of the movement mechanism where the at least one guide tube and at least one injector tube are both advanced. In some embodiments, 2 or more marker lines are included on the proximal handle. In some embodiments, the proximal handle can include a first marker line denoting the position of the movement mechanism where the at least guide tube and at least one injector tube are both retracted, a second marker line denoting the position of the movement mechanism where the at least one guide tube is advanced but the at least one injector tube is retracted and a third marker line denoting the position of the movement mechanism where the at least one guide tube and at least one injector tubes are both advanced. In some embodiments, the proximal handle includes at least one icon associated with the state of the catheter chose from the group of: the position of the movement mechanism where the at least one guide tube and at least one injector tubes are both retracted, the position of the movement mechanism where the at least one guide tube is advanced but the at least one injector tube is retracted, or the position of the movement mechanism where the at least one guide tube and at least one injector tube are both advanced. In some embodiments, the proximal handle includes a first icon denoting the position of the movement mechanism where the at least guide tube and at least one injector tube are both retracted, a second icon denoting the position of the movement mechanism where the at least one guide tube is advanced but the at least one injector tube is retracted and a third icon denoting the position of the movement mechanism where the at least one guide tube and at least one injector tubes are both advanced. In some embodiments, the proximal handle includes two of each of the three icons. In some embodiments, the handle includes at least one flushing port. In some embodiments, the handle includes a finger detent to aid in positioning the operators hand for operating the handle. In some embodiments, the movement mechanism is a slide switch. In some embodiments, there is at least one marker line on the top surface of the handle. In some embodiments, there are at least two marker lines on the top surface of the handle. In some embodiments, the at least one icon is placed in a location chosen from: the top surface of the handle, one of the side surfaces of the handle, both side surfaces of the handle, or a chamfer or filleted surface between the top surface and a side surface of the handle.

In some embodiments, a method for delivery of a fluid outside of the inside wall of a target vessel of a human body is provided. In some embodiments, the method can include advancing into the vessel a catheter. In some embodiments, the catheter can include having a catheter body, a fluid injection lumen, a proximal handle including an unlock mechanism, a longitudinal movement mechanism and distal portion including at least one guide tube having a distal end and at least one injector tube with distal needle located coaxially within the at least one guide tube. In some embodiments, the at least one guide tube is extendable away from the catheter body. In some embodiments, the injector tubes is extendable beyond the distal end of at least one guide tube. In some embodiments, the distal needle of the at least one injector tube has fluid egress in fluid communication with the catheter fluid injection lumen. In some embodiments, the method can include activating the unlock mechanism on the handle. In some embodiments, the method can include operating the longitudinal movement mechanism to advance a preset distance at least one guide tube away from the catheter body until the distal end of the at least one guide tube is in proximity to the inside wall of the vessel. In some embodiments, the unlock mechanism is deactivated when the at least one guide tube is advanced the preset distance. In some embodiments, the method can include re-activating the unlock mechanism. In some embodiments, the method can include operating the longitudinal movement mechanism to extend the at least one injector tube a preset distance beyond the distal end of at least one guide tube, causing the at least one injector tube to penetrate through the inside wall of the target vessel placing the fluid egress of the at least one needle into a volume of tissue outside of the inside wall of the target vessel. In some embodiments, the method can include attaching a fluid source to the catheter. In some embodiments, the method can include injecting fluid through the catheter injection lumen and out of the needle fluid egress into a volume of tissue outside of the inside wall of the vessel.

In some embodiments, the distal portion of the catheter includes three guide tubes and three injector tubes with distal needles. In some embodiments, the method can include re-activating the unlock mechanism. In some embodiments, the method can include operating the longitudinal movement mechanism to retract the at least one injector tube back within the at least one guide tube deactivating the unlock mechanism. In some embodiments, the method can include re-activating the unlock mechanism. In some embodiments, the method can include operating the longitudinal movement mechanism to retract the at least one guide tube with retracted injector tube back within the catheter body deactivating the unlock mechanism.

BRIEF DESCRIPTION OF THE DRAWINGS

FIG. 2 is a side view of an embodiment of the proximal handle designed for use with, for example, the PTAC of FIG. 1.

FIG. 3 shows a close up view of the section 223 of FIG. 2.

FIG. 4 shows a top view of the handle.

FIGS. 5A through 5I illustrate non-limiting steps in a method of using the handle 200 to deploy and retract the guide tubes and injector tubes with needles of the PTAC of FIG. 1.

DETAILED DESCRIPTION

Figure 1:
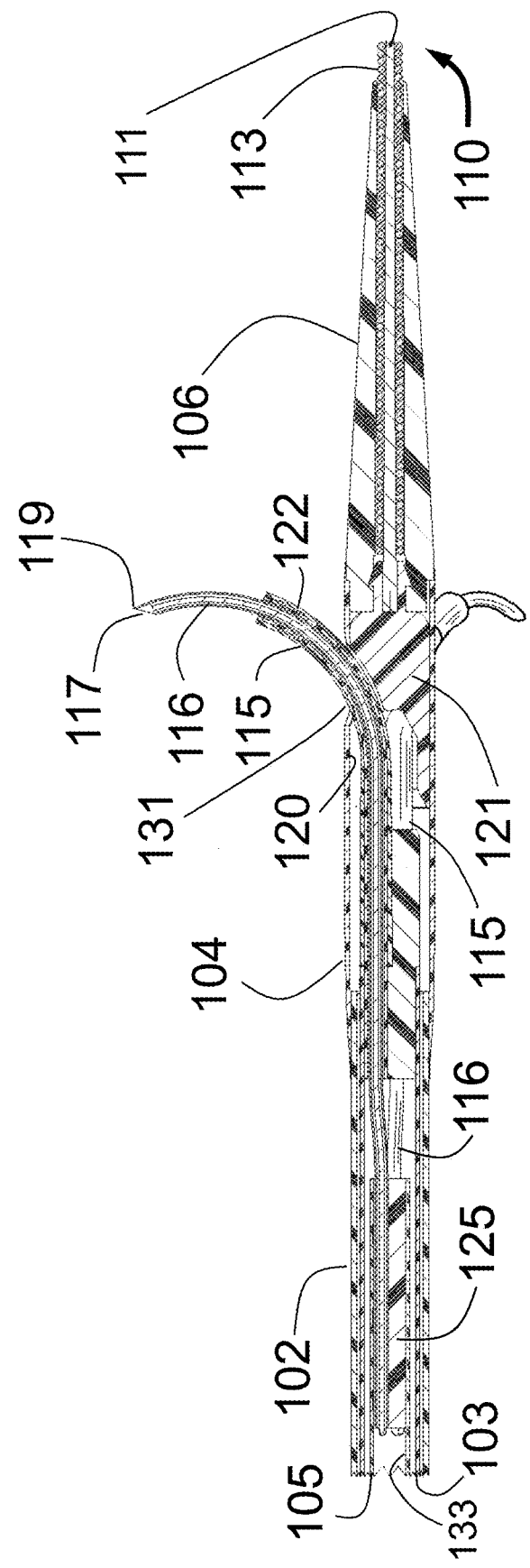
FIG. 1 is a longitudinal cross-section of a distal portion of the prior art PTAC shown in FIG. 3 of Fischell et al. U.S. Pat. Nos. 9,179,962, 9,254,360, 9,301,795, 9320,850, 9,526,827, 9,539,047, and 9,554,849 in its open position as it would be configured for delivery of fluid into a volume of tissue outside of the inside wall of a target vessel.

FIG. 1 is a longitudinal cross-section of a distal portion of a Peri-vascular Tissue Ablation Catheter PTAC 100 as shown in FIG. 3 of Fischell et al. U.S. Pat. Nos. 9,179,962, 9,254,360, 9,301,795, 9320,850, 9,526,827, 9,539,047, and 9,554,849.

FIG. 1 is a longitudinal cross-section of the expanded distal portion. FIG. 1 shows the fully open position with the guide tubes 115 with coaxial injector tubes 116 with sharpened distal injection needles 119 and needle distal opening 117 which is the injection egress deployed outward beyond the distal end of the guide tubes 115. It should be understood there can be any number of injector tubes and guide tubes. The guide tubes 115 are the guiding elements that help support the thin and flexible injector tubes 116. In some embodiments, the injector tubes include injection needles. In some embodiments, the injector tubes include electrodes. In some embodiments, the injector tubes are supported as they are advanced into the wall of a target vessel.

In some embodiments, it is envisioned that a portion of the injector tube(s) 116 and/or a portion of the guide tube(s) 115 are marked with a radiopaque material such as gold or tantalum, or a piece of radiopaque material may be used to form or be located within the injector tubes 116 or the sharpened needles 119 to provide better visualization of the deployment using standard fluoroscopy. FIG. 1 shows a radiopaque wire placed within the injector tube 116 to allow fluoroscopy to be used by the operator to clearly identify the position of the injector tubes 116. The material for the radiopaque wire can be selected from well-known radiopaque metals such as platinum, tantalum or gold or an alloy of that type of metal.

FIG. 1 also shows the memory configuration for the fully opened guide tubes 15. The preformed radius of curvature of the injector tubes 116 can correspond to that of the guide tubes 115 so that the guide tubes 115 will maintain their position against the interior wall of the target vessel as the injector tubes 116 are advanced coaxially there through to penetrate the wall of the target vessel.

Still referring to FIG. 1, also shown is an outer tube 102, outer tube extension 104 having distal openings 131 through which the guide tubes 115 with radiopaque markers 122 are advanced outward from the body of the PTAC 100. Also shown is the tapered section 106 and fixed guide wire 110 with distal tip 109. The injector tubes 116 with distal injection needles 119 and needle distal openings 117 are shown in their fully deployed positions. The openings 131 support the sides of the guide tubes 115 as the guide tubes 115 are advanced outward before the advancement of the injector tubes 16 with distal injector needles 119. The PTAC 100 of FIG. 1 has three guide tubes with the third tube hidden behind the catheter and not visible in this schematic view. Although the PTAC 100 of FIG. 1 has three guide tubes 115, it is envisioned that other embodiments could have as few as one or as many as eight guide tubes or more, with 2, 3, 4, 5, 6, 7, 8, or ranges including any two of the aforementioned values being also possible. A larger diameter target vessel might suggest the use of as many as 4 to 8 or more guide tubes 115 and injector tubes 116.

Different shapes are envisioned for the distal openings (or windows) 131 in the outer tube extension 104 where the guide tubes 115 exit. These possible shapes include a racetrack design with curved (e.g., round) proximal and distal ends and straight sides in the axial direction, and oval or round shapes. It is also envisioned that there could be a movable flap covering the opening 131 or a slit that could be opened to make the outer surface of the PTAC smooth for better delivery into the desired target lumen, such as the renal artery in some cases.

The proximal end of FIG. 1 shows the three concentric tubes, the outer tube 102, middle tube 103 and inner tube 105 which form the central portion and most of the length of the PTAC 100. The outer tube 102 is attached to the outer tube extension 104 which is in turn attached to the tapered section 106. The fixed guide wire 110 with core wire 111 and outer layer 113 extends distally from the distal end of the tapered section 106. It should be noted that only part of the length of the guide wire 110 is shown in FIG. 1.

FIG. 1 shows the guide tube 115 with radiopaque marker 122 in its fully advanced position placed through the opening 131 in the outer tube extension 104. The interior surface of the outer tube extension 104 forms part of the tubular shaft 120 can in some cases be made from a stiff material such as a metal or high durometer plastic so that it will be relatively rigid as the guide tubes 115 are advanced and retracted.

Some embodiments of a PTAC 100 can use a plurality, e.g., four (or two, three, five, or another number) different tubular structures instead of just an outer tube 102 and outer tube extension 104. Specifically, the proximal section could be a first tubular structure, such as a metal hypotube in some cases. The metal hypotube could connect at its distal end to a second tubular structure, such as a relatively stiff plastic tube about 20 cm long or more or less that would in turn connect to a third tubular structure, such as a softer more flexible plastic tube about 10 cm long or more or less which connect to the fourth tubular structure, which could be the tube 102 shown in FIG. 1. Other number of tubular structures are contemplated, includes tubular structures of the same or different length, and/or the same or different materials. The plastic tubes can have the same inner and outside diameters in some cases. The outer tube extension 104 which is the distal end section of the catheter body typically has a slightly larger inside diameter than the soft outer tube 102, such as no more than about 20%, 15%, 10%, 5%, 3%, 2%, 1%, larger in inside diameter, or ranges incorporating any two of the aforementioned values. The manifold 125 that connects the inner tube 105 to the injector tubes 116 is coaxially within the plastic tubes and at least several centimeters proximal to the outer tube extension 104 which is the distal end section of the catheter body of the PTAC 100.

In a preferred embodiment, the middle tube 103 attaches to, a proximal metal hypotube and the inner tube 105 would also attach to proximal portion formed from a metal hypotube.

The central buttress 121 shown in FIG. 1, which can be a mechanical, non-expandable, non-inflatable central buttress in some cases, supports the guide tube 115 both as it is pushed distally and after it is fully deployed. This central buttress 121 also provides radial support for the advanced guide tubes 115 that prevents the guide tubes 115 from backing away from the interior wall of the target vessel as the injector tubes 116 are advanced through the guide tubes 115 forward to their desired position, e.g., about 2-4 mm beyond the interior wall of the target vessel. In exceptional cases, the injection needles 119 at the distal ends of the injector tubes 116 might be advanced as deep as 8 mm or more beyond the interior wall of the target vessel. Additional lateral support for the guide tubes 115 is provided by the sides of the openings 131 that in combination with the central buttress 121 can be highly advantageous to the radial and circumferential/lateral support both during guide tube 115 advancement and outward expansions, and as backup during delivery of the injection needles 119 through the interior wall of the target vessel. The buttress may comprise a deflection surface such as a curved or linear ramp, which may in a curved embodiment correspond to the radius of curvature of the distal surface of the guide tube 115. The guide tubes 115 can slide along a deflection surface such as the curved ramp 144 of the central buttress 121 (shown in FIG. 4) as they are pushed. The guide tubes 115 advance toward the distal end of the PTAC 100 toward the openings 131. The guide tubes 115 can interact with a deflection surface such as the curved ramp 144 of the central buttress 121 as they are guided toward the openings 131.

The preformed radius of curvature of the injector tubes 116 can be similar to that of the guide tubes 115 so that the guide tubes 115 will maintain their position against the interior wall of the target vessel as the injector tubes 116 are advanced to penetrate the interior wall of the target vessel. Specifically, the radius of curvature of the central axis of the distal portion of the injector tube 116 can be approximately the same as the radius of curvature of the central axis of the guide tube 115. In some embodiments, the guide tubes have atraumatic, blunt distal ends such that they are not configured to penetrate through the interior wall of the target lumens.

As seen in FIG. 1 the inner tube 105 with fluid injection lumen 133 connects through the manifold 125 to the three injector tubes 116, thus the lumens of the injector tubes 116 are in fluid communication with the lumen 133. The inner tube 105 and manifold 125 can slide along the longitudinal axis of the PTAC 100 inside of the middle tube 103 which is shown with uniform diameter over its length including the portion coaxially outside of the manifold 125.

The manifold 125 is located within the lumen of the inner tube 105 in a portion of the tube 105 that is proximal to the distal end of the tube 105. The inner tube 105 and manifold 125 are both located coaxially within the outer tube 102 of the PTAC 100 at a position proximal to the outer tube extension 104 which is the distal end section of the outer body of the PTAC 100.

The proximal end of the injector tube 116 is in fluid communication with the injection lumen 133 of the inner tube 105. Longitudinal motion of the inner tube 105 within the uniform diameter middle tube 103 causes the manifold 125 and attached injector tubes 116 to also move longitudinally. This longitudinal motion caused by control mechanisms near the proximal end of the PTAC 100 will advance and retract the injector tubes 116 through the lumens of the guide tubes 115 to expand outwardly to penetrate the wall of the target vessel to facilitate delivery of the ablative fluid.

The guide tube connector 132 connects the three guide tubes 115 to the middle tube 103 that provides the impetus for advancement and retraction of the three guide tubes 115. The motion of the middle tube 103 is produced by the motion of control mechanisms at the proximal end of the PTAC 100. The manifold 125 lies inside of the distal portion of the inner tube 105 and connects together the three injector tubes 116 so that advancement and retraction of the inner tube 105 provides simultaneous advancement and retraction of the injector tubes 116. Also shown are the flushing spaces between the several tubes. Specifically shown is the outer annular space between the middle tube 103 and the outer tube 102 and the inner annular space between the inner tube 105 and the middle tube 103. Each of these spaces is to be flushed through with normal saline solution prior to insertion of the PTAC 100 into the patient's body.

The guide tubes 115 and guide tube connector 132 are attached coaxially within the distal section of the middle tube 103. Thus longitudinal motion of the middle tube 103 will cause longitudinal motion of the guide tube connector 132 and guide tubes 115 thus allowing the mechanism at the proximal section of the PTAC 100 to advance and retract the guide tubes 115 with respect to the outer tube 102 and outer tube extension 104. The guide tube connector 132 and connects together the three guide tubes 115 so that advancement and retraction of the middle tube 103 provides simultaneous advancement and retraction of the guide tubes 115.

In some embodiments, a penetration depth limitation could be a mechanism that limits the forward motion of the distal end of the inner tube 105 with respect to the guide tube connector 132. In some embodiments, a penetration depth limitation can be a mechanism at the proximal section of the PTAC 100, such as distinct positions of the slider as described herein.

In some embodiments, one or more components of the PTAC 100 are typically made from plastic materials such as polyamide, polyurethane, nylon or tecothane. These include the outer tube 102, middle tube 103 and inner tube 105, the outer tube extension 104, inner layer and/or outer layer of the guide tubes 115, the tapered section 106, the buttress 121, the guide tube connector 132 and the manifold 125. The manifold 125 can be a molded part or be epoxy or another resin that is injected to glue the injector tubes together within the lumen of the inner tube 105. It is also envisioned that any or all of the inner tube 105, middle tube 103 or outer tube 102 could also be a metal hypotube or a metal reinforced plastic tube. The injector tubes 116 would typically be made of a springy or shape memory metal such as nitinol. The radiopaque wire 118 and guide tube radiopaque marker 122 would be made of a radiopaque material such as gold, platinum or tantalum or an alloy of these or similar metals.

FIG. 2 is a side view of an embodiment of the control handle 200 designed for use with the PTAC 100 of FIG. 1. The handle 200 can be designed to simplify the operation of the PTAC 100 while including appropriate failsafe features.

The main body 210 of the handle 200 can be any shape. In the illustrated embodiment, the main body 210 is of relatively rectangular or rounded cross section with beveled or rounded edges where the side surface of the handle 211 meets the bottom of the handle 215. A finger detent 212 can be provided to improve the comfort of holding the handle 200 and is positioned so that the operator's hand is situated to be able to best operate the primary controls of the handle 200. The controls of the handle 200 can include the unlock button 222, the unlock release button 226, and the slider 224. The slider 224 is an example of a longitudinal movement mechanism that can advance and retract the PTAC 100 guide tubes 115 of FIG. 1 with respect to the PTAC 100 catheter body and can also advance and retract the PTAC 100 injector tubes 116 with needles 119 with respect to the guide tubes 115. Controls could include, for example, buttons, dials, switches, sliders, and the like.

In some embodiments, the release button 226 is optional. In some embodiments, the release button 226 is a manual lock of the unlock button 222. In some embodiments, the release button 226 is a manual lock of the slider 224. In some embodiments, the unlock button 222 is a switch or toggle such that the user can move between the locked and the unlocked state. In some embodiments, the unlock button 222 can be pushed down or pulled up such that the user can move between the locked and the unlocked state. In some embodiments, the unlock button 222 can automatically pop up when released. In some embodiments, the unlock button 222 can remain depressed when depressed. In some embodiments, the release button 226 is distal to the unlock button 222 which is in turn distal to the slider axially along the main body 210 of the handle 200 as shown. Other configurations are contemplated which enable the unlock button 222 to be in a locked state and an unlocked state.

As described herein, the slider 224 can sequentially deploy the guide tubes 115 first and the injector tubes 116 second. As described herein, the slider 224 can also sequentially retract the injector tubes 116 first and the guide tubes 115 second. As described herein, the slider 224 can deploy and retract all guide tubes 115 simultaneously. As described herein, the slider 224 can deploy and retract all injector tubes 116 simultaneously.

As described herein, the slider 224 can engage the manifold 125 that connects the inner tube 105 to the injector tubes 116. The slider 224 can move the manifold forward and backward to deploy the injector tubes 116. As described herein, the slider 224 can engage the guide tube connector 132 that connects the middle tube 103 to the guide tubes 115. The slider 224 can move the guide tube connector 132 forward and backward to deploy the guide tubes 115. The three guide tubes 115 are attached to each other near their proximal ends by the guide tube connector 132.

The unlock button 222 can include locked and unlocked states. In some embodiments, the unlock button 222 can be depressed such that the unlock button 222 is up when locked and down when unlocked. When depressed and released the unlock button 222 can stay in the unlocked (down) state and can allow longitudinal motion of the slider 224. If the operator depresses the unlock button 222 in error and wishes to pop it back up returning it to the locked (up) state, this can be accomplished by depressing the unlock release button 226.

In some embodiments, the unlock button 222 can allow movement of the slider 224 in the unlocked state and prevent movement of the slider 224 in the locked state. In some embodiments, the unlock button 222 can stay in the unlocked state until movement of the slider 224 causes the unlock button to enter the locked state. In some embodiments, the unlock button 222 can stay in the unlocked state until the release button 226 is depressed. In some embodiments, the unlock button 222 can stay in the locked state until the unlock button 22 is depressed. In some embodiments, the unlock button 222 can be overridden by continuously depressing the unlock button 222 such that the unlock button 222 does not enter the locked state. Other configurations are contemplated.

In some embodiments, the operator can activate the unlock button 222 on the handle such as by depressing the unlock button 222. In some embodiments, the operator can move the slider 224 in a distal direction to advance at least one guide tube away from the catheter body until the distal end of the at least one guide tube is in proximity to the inside wall of the vessel. In some embodiments, the slider 224 will move a preset distance. In some embodiments, the slider 224 will cause the at least one guide tube to move a preset distance. In some embodiments, the unlock button 222 is deactivated when the at least one guide tube is advanced by the slider 224. In some embodiments, the unlock button 222 is unlocked when the at least one guide tube is advanced by the slider 224. In some embodiments, motion of the slider 224 causes the unlock button 222 to enter the locked state. In some embodiments, motion of the slider 224 causes the unlock button 222 to automatically pop up. In some embodiments, the slider 224 moves stepwise only between preset stops as described; in other embodiments, the slider 224 can move continuously through a working range.

In some embodiments, the operator can re-activate the unlock button 222, such as by depressing the unlock button 222. In some embodiments, the operator can move the slider 224 to extend the at least one injector tube beyond the distal end of at least one guide tube. In some embodiments, the slider 224 will move a preset distance. In some embodiments, the slider 224 will cause the at least one injector tube to move a preset distance. In some embodiments, the slider 224 will cause the at least one injector tube to penetrate through the inside wall of the target vessel. In some embodiments, the slider 224 will place the fluid egress of the at least one needle into a volume of tissue outside of the inside wall of the target vessel. In some embodiments, the operator can attach a fluid source to the catheter. In some embodiments, the operator can inject fluid through the catheter injection lumen and out of the needle fluid egress into a volume of tissue outside of the inside wall of the vessel. In some embodiments, motion of the slider 224 causes the unlock button 222 to enter the locked state.

In some embodiments, the operator can re-activate the unlock button 222, such as by depressing the unlock button 222. In some embodiments, the operator can move the slider 224 to retract the at least one injector tube into the distal end of at least one guide tube. In some embodiments, motion of the slider 224 causes the unlock button 222 to enter the locked state.

In some embodiments, the operator can re-activate the unlock button 222, such as by depressing the unlock button 222. In some embodiments, the operator can move the slider 224 to retract the at least one guide tube into the catheter body. In some embodiments, motion of the slider 224 causes the unlock button 222 to enter the locked state.

In some embodiments, the marker indicia lines 232, 234, and 236 with corresponding catheter state icons 242, 244, and 246 can indicate positions of the slider 224. In some embodiments, the marker lines 232, 234, and 236 with corresponding catheter state icons 242, 244, and 246 can indicate positions wherein the unlock button 222 enters the locked state. In some embodiments, the marker lines 232, 234, and 236 with corresponding catheter state icons 242, 244, and 246 can indicate positions wherein further movement of the slider 224 is prevented by the unlock button 222 until the unlock button 222 is activated such as by depressing the unlock button 222. In some embodiments, the unlock button can maintain the position of the slider 224, and thus the guide tubes. In some embodiments, the unlock button can maintain the position of the slider 224, and thus the injector tubes. In some embodiments, the slider 224 can have exactly three positions corresponding to the three indicia shown in FIGS. 5A-5I.

The controls of the handle 200 including the unlock button 222, the unlock release button 226, and the slider 224 can be placed on the upper side of the handle 200. The controls can face the user when the user grips the handle 200. The upper side of the handle 200 includes a rounded or beveled surface 208. A relock button or unlock release button 226 can be placed on the top surface of the handle 200. The controls of the handle 200 including the unlock button 222, the unlock release button 226, and the slider 224 can be placed in any order. In the illustrated embodiment, release button 226 is distal to the unlock button 222. In the illustrated embodiment, unlock button 222 is distal to the slider 224. Other arrangements are contemplated such as any order, coaxial, offset, etc.

Distal to the main body 210 is a tapered section 206. Distal to the tapered section 206 is a strain relief section 204 which is outside of the outer tube 102 of PTAC 100 shown in FIG. 1.

Proximal to the main body 210 is the proximal tapered section 214. Proximal to the proximal tapered section 214 is a connector 202 for attaching a syringe (not shown) or other fluid dispensing mechanism. The connector 202 can be a standard Luer or Luer lock connector or it may be a non-standard connector. The lumen of the connector 202 is in fluid communication with the lumen 133 of the inner tube 105 of the PTAC 100 of FIG. 1. A flushing tube 252 with Luer connector 254 is in fluid communication with two spaces: 1) the space between the inner tube 105 and middle tube 103 and 2) the space between the middle tube 103 and outer tube 102 shown in FIG. 1 and used to flush the catheter with saline before operation of the PTAC 100.

FIG. 3 shows a close up view of the section 223 of FIG. 2 with the unlock button 222, the release button 226, and the slider 224. Also shown are the marker lines 232, 234, and 236 with corresponding catheter state icons 242, 244, and 246. These marker lines and catheter state icons are placed to clearly show the operator the current state of the PTAC 100 distal end. The marker line 232 corresponds to the closed position of the PTAC 100 as illustrated by the icon 242. The marker line 234 corresponds to the PTAC 100 position where the guide tubes 115 are deployed but the injector tubes 116 with needles 119 are still retracted. The icon 244 illustrates this position. The marker line 236 corresponds to the PTAC 100 position where the guide tubes 115 are deployed and the injector tubes 116 with needles 119 deployed as shown in FIG. 1. The icon 246 illustrates this state. The marker lines 232, 234 and 236 and the catheter state icons 242, 244 and 246 may be etched, engraved or printed onto the surface 208, or presented on one or more displays in some embodiments. The slider 224 can align with the marker lines and catheter state icons at various stages of operation of the PTAC 100. The distal edge of the slider 224 can align with the marker line 232 when the PTAC 100 is closed. The distal edge of the slider 224 can align with the marker line 234 when the guide tubes 115 are deployed. The distal edge of the slider 224 can align with the marker line 236 when the injector tubes 116 are deployed. In the illustrated embodiment, the icons are pictorial shapes that illustrate the shape of the catheter. Other icons are completed, e.g., shapes, words, letters, numbers, indicia, images, colors, etc. In some embodiments, instead or in addition of visual indicia, moving the slider 224 could result in audible and/or tactile (e.g., haptic) feedback to alert the operator to the different slider 224 positions.

FIG. 4 shows a top view of the handle 200 looking down on the top surface 218 of the handle 200. FIG. 4 shows the main body 210, with top surface 218, outer tube 102 of the PTAC 100 of FIG. 1, distal tapered section 206, strain relief section 204, proximal tapered section 214, connector 202, buttons 226 and 222, slider 224, and marker lines 232, 234 and 236. The catheter state icons are shown but not labeled.

It can be seen that between the side surface of the handle 211 of FIG. 2 and the top surface 218 of the handle 200 are the rounded (filleted) or beveled (chamfered) surfaces 208 and 209. The advantage of a beveled or rounded surface in some cases is to allow visualization of at least one set of catheter state icons 242, 244 and 246 if the handle 200 is operated either with the top side 218 up or with either side (such as 211) of the main body facing up. If a bevel rather than a rounded (filleted) edge is used, in some embodiments, an angle of 10 to 80 degrees may function but an angle closer to 45 degrees may be optimal.

FIGS. 5A through 5I illustrate stages of some embodiments of a method of using the handle 200 to deploy and retract the guide tubes 115 and injector tubes 116 with needles 119 of the PTAC 100 of FIG. 1 where the distal end configurations are shown in FIG. 8 through 10 of U.S. Pat. Nos. 9,179,962, 9,254,360, 9,301,795, 9320,850, 9,526,827, 9,539,047, and 9,554,849.

Some embodiments of a method for using the handle 200 after the PTAC 100 disclosed here can begin after one or more of the following:

1. the PTAC is removed from its package,
2. flushed with saline or other media,
3. the injection lumen 133 of FIG. 1 has been filled with the fluid,
4. the PTAC 100 is placed in its closed configuration as shown, for example, in FIG. 8 of Fischell et al. U.S. Pat. Nos. 9,179,962, 9,254,360, 9,301,795, 9320,850, 9,526,827, 9,539,047, and 9,554,849 with the handle controls as shown in FIG. 5A. In some embodiments, all or just some of the steps are performed. In some embodiments, the steps that are performed are performed in the order above, or a different order.

The steps for use of the device to deliver a fluid outside of the inside wall of a target vessel can include one or more of the following:

1. In the closed configuration of FIG. 5A where the distal end of the slider 224 is aligned with the marker line 232, the PTAC 100 is delivered to the desired site in the human body.
2. The operator depresses the unlock button 222 and releases it. The button 222 will then stay depressed in the unlock position. This permits distal movement of the slider 224 which is advanced distally until it comes to a stop at the marker line 234 and the unlock button of the handle 200 automatically pops back up relocking the slider 224 in this position as shown in FIG. 5C. Here the icon 244 indicates to the operator that the guide tubes 115 have been deployed as shown in FIG. 9 of Fischell et al. U.S. Pat. Nos. 9,179,962, 9,254,360, 9,301,795, 9320,850, 9,526,827, 9,539,047. The operator then can confirm the guide tubes 115 are deployed by angiography or another imaging technique.
3. The PTAC 100 injector tubes 116 with needles 119 of FIG. 1 for example can be deployed by depressing the unlock button 222 as in step 2 and advancing the slider 224 distally until the slider 224 comes to a stop as shown in FIG. 5E with the slider's 224 distal end aligned with marker line 246. The unlock button 222 once again pops back up relocking the slider 224 in place. In this state, the PTAC 100 injector tubes 116 with needles 119 are fully deployed as indicated by the icon 246 and as shown in FIG. 10 of Fischell et al. U.S. Pat. Nos. 9,179,962, 9,254,360, 9,301,795, 9320,850, 9,526,827, 9,539,047. The operator then can confirm the injector tubes 116 are deployed by angiography or other imaging techniques.
4. A fluid source (e.g. a syringe not shown) is attached to, e.g., the connector 202 of FIGS. 2 and 4 and the fluid is delivered through the needles 119 into the desired location in the human body.
5. The fluid source is removed from the connector 202 of FIGS. 2 and 4.
6. The operator then depresses and releases the unlock button 222 as shown in FIG. 5F and retracts the slider 224 in the proximal direction until distal end of the slider 224 reaches marker line 234 as seen in FIG. 5G where it will stop and the unlock button 222 will pop up relocking the mechanism. This step retracts the PTAC 100 injector tubes 116 with needles 119 whose state with guide tubes 115 deployed is shown, for example, in FIG. 9 of Fischell et al. U.S. Pat. Nos. 9,179,962, 9,254,360, 9,301,795, 9320,850, 9,526,827, 9,539,047 corresponding to the icon 244.
7. The operator once again will depress and release the unlock button 222 which will remain in the unlocked position as shown in FIG. 5H. The operator can then retract the slider 224 proximally until the distal end of the slider 224 is aligned with marker line 232 as shown in FIG. 5I putting the PTAC 100 back where it began in step 1 in its closed position corresponding to the icon 242. In some embodiments, all steps or just some of the steps are performed. In some embodiments, the steps that are performed are performed in the order above, or a different order.

It is envisioned that an additional feature of a handle according to some embodiments is that it allows the operator to go from (using one or two hands) the state of FIG. 5E to the state of FIG. 5I by holding down the unlock button 222 so that it will not pop up and retracting the slider 224 from having its distal end aligned with marker line 236 all the way back until the slider distal end is aligned with marker line 232. Using 2 hands, the operator can use one finger to depress the unlock button 222 and use another finger (e.g., of the same or a different hand) to slide the slider 224 proximally.

While one could by holding down the unlock button 222 go sequentially from FIG. 5A through FIGS. 5B, 5C and 5D to 5E in some embodiments, this method may not be recommended in some cases.

Figure 6:
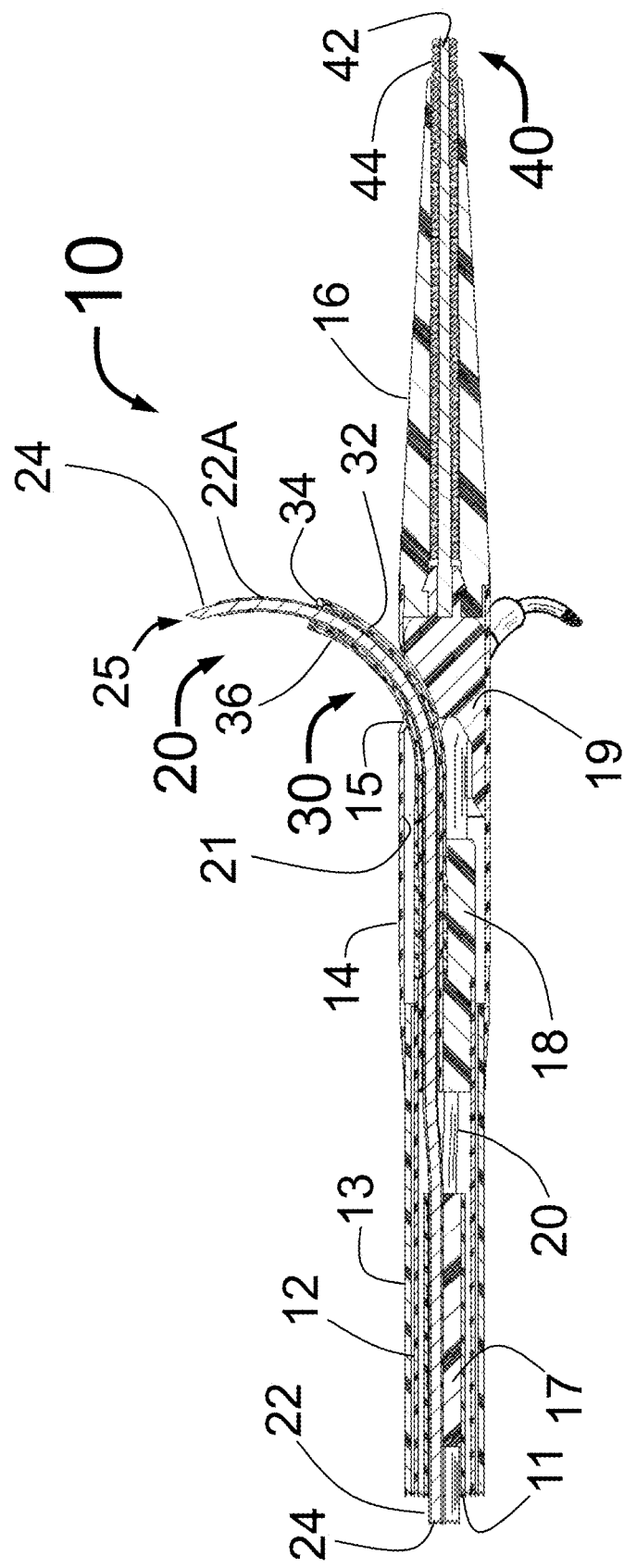
FIG. 6 is a longitudinal cross-section of a distal portion of the prior art SNSC/PNASC 10 as shown in FIG. 2 of U.S. Pat. Nos. 9,931,046 and 9,949,652.

Fischell et al. in U.S. Pat. Nos. 9,931,046 and 9,949,652 describe a Sympathetic Nerve Sensing Catheter (SNSC) and a Peri-vascular Nerve Ablation and Sensing Catheter (PNASC) that can be used for sensing nerve activity, stimulating nerve activity, and/or ablating nerve activity by chemical or energy ablation. FIG. 6 is a longitudinal cross-section of a distal portion of the prior art SNSC/PNASC 10 as shown in FIG. 2 of U.S. Pat. Nos. 9,931,046 and 9,949,652, which are hereby incorporated by reference in their entireties.

FIG. 6 is a schematic view of the distal portion of a Nerve Sensing Catheter (NSC) 10 that is designed to sense energy from extra-vascular tissue within a human body, stimulate with electrical energy, and/or deliver electrical energy to tissue, for example, to provide for obtaining and assessing evoked activity. The NSC 10 is shown in its open position, showing an inner tube 11, middle tube 12, outer tube 13, outer tube extension 14 having distal openings 15 through which the guide tubes 30 with radiopaque markers 36, distal tip 34 and outer layer 32 are advanced outwardly from the body of the NSC 10. Also shown is the tapered section 16 and fixed guide wire 40 with distal tip 42. The NSC includes three conduits 20 with outer insulation 22, and sharpened wire 24, with 2 of the three guide tubes and conduits shown in their fully deployed positions (the third is not shown). The sharpened wires 24 can be made from or coated with a radiopaque material such as gold or platinum.

The conduits 20 run all the way to the proximal end of the NSC 10 where they interface with electronic equipment 500 that provides energy. The distal tips 24 of the conduits 20 are shown here in the distal portion of the NSC 10. The conduits 20 extend through the catheter body within the lumen of the inner tube 11. In some embodiments, the insulation 22 that insulates the conduits within the catheter body does not extend around the most distal portion of the conduit 20 since this portion terminates as a sharpened wire/needle 24 which will penetrate the vascular wall and can act as an electrode.

The openings 15 in the distal portion of the catheter support the guide tubes 30 as the guide tubes 30 are advanced outwardly in order to provide structural support during the subsequent deployment of the sharpened wire 24. Although the NSC 10 of FIG. 6 has three guide tubes 30, it is envisioned that other embodiments could have as few as one or as many as eight or more guide tubes (e.g., 1, 2, 3, 4, 5, 6, 7, 8, or more, or ranges including any two of the aforementioned values) with an optimum number typically being three or four in the case of renal denervation. A larger diameter target vessel might suggest the use of as many as 4 to 8 guide tubes 30 and conduits 20.

In addition to providing electrical conductivity from the proximal end of the NSC to the distal sharpened wires 24, the conduits 20 may be adapted to be hollow to also provide a passageway for fluid injection near the tip of the sharpened wires 24. A modified version of the NSC is disclosed herein, that provides both nerve sensing and nerve ablation capabilities. This dual function catheter will be called a Perivascular Nerve Ablation and Sensing Catheter (PNASC). The catheters described herein can provide one or more of the following:

Provide both electrical sensing and stimulation using the sharpened wires 24 which act as electrodes to both sense nerve activity and provide energy to tissue;

Provide electrical energy such as RF to the sharpened wires 24 that act as electrodes provide energy based ablation;

Have a fluid passageway in the conduits 20 with an egress near the distal end of the sharpened wires 24 for injection of an ablative fluid for chemical nerve ablation and or dispensing an anesthetic/analgesic agent such as lidocaine; and/or Provide an ultrasound transducer either within the body of the PNASC or in the distal portion of the conduits 20 to provide energy based ablation, such as ablation at perivascular sites that is delivered by the conduits 20.

Different shapes are envisioned for the distal openings (or windows) 15 in the outer tube extension 14 where the guide tubes 30 exit. These possible shapes include and oval or round shapes such as a racetrack design with curved (e.g., round) proximal and distal ends and straight sides in the axial direction. It is also envisioned that there could be a movable flap (not shown) covering each opening 15, or a slit that could be opened to make the outer surface of the NSC smooth for better delivery through a guiding catheter into the renal artery. Such a movable flap could be operated under the control of the catheter handle in the proximal section of the catheter. The mechanical operation of the catheter can function so that the flaps are retracted prior to the guide tubes 30 being deployed. Alternatively the flaps may be made flexible and soft enough that these are simply pushed aside by the guide tubes 30 upon deployment.

It can be a feature of some embodiments of the invention that the guide tubes 30 serve as needle or conduit guiding elements that provide structural support for the ultra-thin conduits 20. The three conduits 20, sensors 24 and guide tubes 30 are spaced uniformly around the circumference of the catheter 10 at approximately 120 degrees separation. The uniform spacing improves the sensing performance of the NSC 10. It is also envisioned that the spacing might be non-uniform for example two might be 50 degrees while the third could be 155 degrees from either of the first two. In an alternative embodiment, a catheter for sensing the activity from nerves outside of the lumen of a target vessel of a human body can only include one conduit 20. For the single conduit 20 embodiment, a portion of the body of the NSC 10 such as the outer tube extension 14 will typically be pushed against the inside wall of the artery diametrically opposed to the contact point where the needle guiding element/guide tube 30 expands outward to contact the wall of the artery.

The proximal end of FIG. 6 shows the three concentric tubes, the outer tube 13, middle tube 12 and inner tube 11 which form the central portion of the SNSC/PNASC 10. The outer tube 13 is attached at its distal end to the outer tube extension 14 which is in turn attached to the tapered section 16. The fixed guide wire 40 with core wire 42 and outer layer 44 extends distally from the distal end of the tapered section 16.

FIG. 6 shows the guide tube 30 with outer layer 32, distal tip 34, and radiopaque marker 36 in its fully deployed position as advanced through the opening 15 in the outer tube extension 14. The interior surface of the outer tube extension 14 forms part of the tubular shaft 21. In some embodiments, the tubular shaft 21 is preferably made from a stiff material such as a metal or high durometer plastic so that it will be relative rigid as the guide tubes 30 are advanced and retracted.

Coaxially within the lumen of the guide tube 30 is the insulated wire 20 with insulated outer layer 22A and core wire 24. As described herein, in some embodiments, the core wire 24 is hollow allowing for the delivery of fluids, and in some embodiments the core wire 24 is solid. The uninsulated distal portion of the wire 20 forms the electrode 25. The electrode 25 can act as a sensor that in combination with either or both of the other two electrodes 25 at the ends of the other two sharpened wires 20, or with a remote electrode in electrical communication with the patient. The electrode 25 can be used to measure activity of the sympathetic nerves in the perivascular space outside of the renal artery. The electrode 25 can be used to stimulate nerves. The electrode 25 can be used to deliver energy to ablate nerves.

The central buttress 19 shown in FIG. 6, supports the guide tube 30 both as it is pushed distally and after it is fully deployed. This central buttress 19 also provides radial support for the advanced guide tubes 30 that prevents the guide tubes 30 from backing away from the interior wall of the target vessel as the sharpened wires 20 are advanced through the guide tubes 30 forward to their desired position in the peri-adventitial space 2-10 mm beyond the interior wall of the target vessel. Additional lateral support for the guide tube 30 is provided by the sides of the openings 15 that in combination with the central buttress 19 provide both radial and circumferential/lateral support both during guide tube 30 advancement and outwardly expansion as well as providing backup during delivery of the wires 20 through the interior wall of the target vessel. The buttress may comprise a deflection surface such as a curved or linear ramp, which may in a curved embodiment correspond to the radius of curvature of the outer surface of the guide tube 30.

Another possible feature of the SNSC/PNASC 10 is that each sharpened wire 20 has a central axis with the same, or nearly the same, radius of curvature as the central axis of the corresponding guide tube 30 when measured in an unconstrained state. In addition, the length of the guide tubes 30 is preferably at least as long as the distal curved portion of the sharpened wires 20. This design constrains the curved portion of each sharpened wire 20 within the lumen of the guide tube 30 so that the sharpened wire 20 cannot twist or change position.

As seen in FIG. 6 the cylinder or manifold 17 attaches the inner tube 11 to the three sharpened wires 20. The cylinder can be formed of any material such as plastic. The inner tube 11 and cylinder 17 can slide along the longitudinal axis of the SNSC/PNASC 10 inside of the middle tube 12. The middle tube is shown with uniform diameter over its length including the portion coaxially outside of the cylinder 17.

Some embodiments of the SNSC/PNASC 10 uses four different tubular structures instead of just an outer tube 13 and outer tube extension 14. Specifically, the proximal section can be a metal hypotube. The metal hypotube can connect at its distal end to a relatively stiff plastic tube about 20 cm long that would in turn connect to a softer more flexible plastic tube about 10 cm long which can be the tube 13 shown in FIG. 6.

In a preferred embodiment, the middle tube 12 attaches to, a proximal metal hypotube and the inner tube 11 would also attach to a proximal portion formed from a metal hypotube. The SNSC/PNASC 10 and the PTAC 100 can have any features described herein, and/or any features described in the patents which are incorporated by reference.

Figure 7:
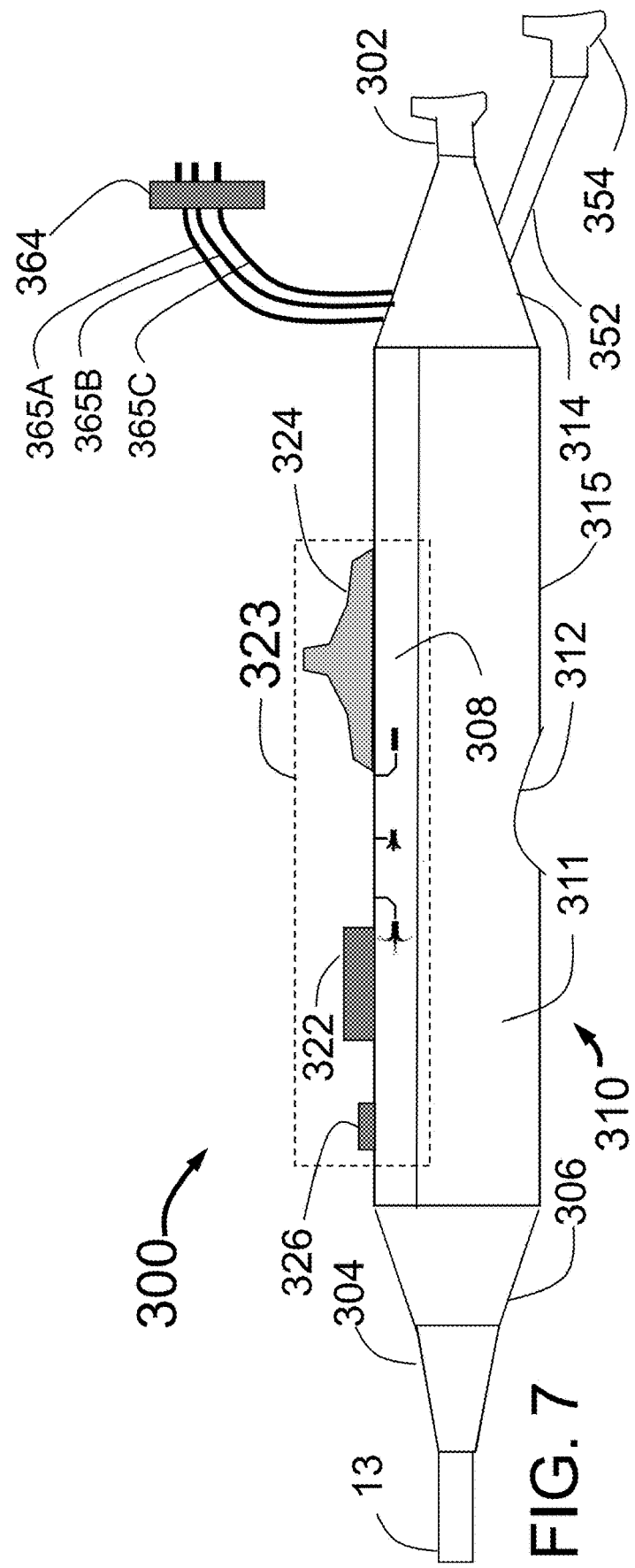
FIG. 7 is a side view of an embodiment of the proximal handle designed for use with the SNSC/PNASC of FIG. 6.

FIG. 7 is a side view of some embodiments of the control handle 300 designed for use with the SNSC/PNASC 10 of FIG. 6. The handle 300 can be designed to simplify the operation of the SNSC/PNASC 10 while including appropriate failsafe features. The control handle 200 and the control handle 300 can have any of the features described herein.

The main body 310 of the handle 300 can include any shape. The main body 310 is configured to be gripped by at least one hand of the operator of the device. The main body 310 can be of relatively rectangular or rounded cross section with beveled or rounded edges where the side surfaces of the handle 311 meets the bottom of the handle 315. In some embodiments, a finger detent 312 improved the comfort of holding the handle 300 and is positioned so that the operator's hand is situated to be able to best operate the primary controls of the handle including an unlock button 322, an unlock release button 326 and a slider 324. The slider 324 is an example of a longitudinal movement mechanism that can advance and retract the SNSC/PNASC 10 guide tubes 30 of FIG. 6 with respect to the SNSC/PNASC 10 catheter body and can also advance and retract the SNSC/PNASC 10 wires 20 with respect to the guide tubes 30.

The unlock button 322 has locked (up) and unlocked (down) states. When depressed and released the unlock button 322 can stay in the unlocked (down) state, which can allow the operator to engage in longitudinal motion of the slider 324. If the operator depresses the unlock button 322 in error and wishes to pop it back up returning it to the locked (up) state, this can be accomplished by depressing the unlock release button 326.

Also shown are the marker lines with corresponding catheter state icons. These marker lines and catheter state icons are placed to clearly show the operator the current state of the SNSC/PNASC 10 distal end. One marker line corresponds to the closed position of the SNSC/PNASC 10. One marker line corresponds to the SNSC/PNASC 10 position where the guide tubes 30 are deployed but the wires 20 with electrodes 25 are still retracted. One marker line corresponds to the SNSC/PNASC 10 position where the guide tubes 30 are deployed and the wires 20 with electrodes 25 are deployed as shown in FIG. 6. The marker lines and the catheter state icons may be etched, engraved or printed onto the handle 200. The slider 324 can align with the marker lines and catheter state icons at various stages of operation of the SNSC/PNASC 10. In the illustrated embodiment, the icons are pictorial shapes that illustrate the shape of the catheter. Other icons are completed, e.g., shapes, words, letters, numbers, indicia, images, colors, etc. as well as other non-visual indicia as described elsewhere herein.

The upper side of the handle 300 includes a rounded or beveled surface 308. A relock button or release button 326 is also placed on the top of the handle 300. Distal to the main body 310 is a tapered section 306, and distal to that is a strain relief section 304 which is outside of the outer tube 13.

Proximal to the main body 310 is the proximal tapered section 314. Proximal to the proximal tapered section 314 is a connector 302 for attaching a syringe (not shown) or other fluid dispensing mechanism. The connector 302 may be a standard Luer or Luer lock connector or it may be a non-standard connector. The lumen of the connector 302 is in fluid communication with the lumen 333 of the inner tube 11 of the SNSC/PNASC 10 of FIG. 6. A flushing tube 352 with Luer connector 354 is in fluid communication with two spaces: 1) the space between the inner tube 11 and middle tube 12 and 2) the space between the middle tube 12 and outer tube 13 shown in FIG. 6 and used to flush the catheter with saline before operation of the SNSC/PNASC 10.

FIG. 7 also shows the externalization of the wires 365A through 365C used to connect external equipment to the wires 20 of FIG. 6. Each wire 365A-365C can connect to an independent electrode. In some embodiments, the wire 365A connects to the electrode 25 of a first wire 20, the wire 365B connects to the electrode 25 of a second wire 20, and/or the wire 365C connects to the electrode 25 of a third wire 20. The wires 365A-365C can be connected to external equipment 364. As described herein, the external equipment 364 can be for sensing electrical energy, stimulating with electrical energy and/or supplying electrical energy. Other energy modalities such as magnetic, ultrasound, vibrational, thermal, or cryo energy sources can be applied alone or in combination.

In some embodiments, the unlock button 322 can allow movement of the slider 324 in the unlocked state and prevent movement of the slider 324 in the locked state. In some embodiments, the unlock button 322 can stay in the unlocked state until movement of the slider 324 causes the unlock button to enter the locked state. In some embodiments, the unlock button 322 can stay in the unlocked state until the release button 326 is depressed. In some embodiments, the unlock button 322 can stay in the locked state until the unlock button 322 is depressed. In some embodiments, the unlock button 322 can be overridden by continuously depressing the unlock button 322 such that the unlock button 322 does not enter the locked state. Other configurations are contemplated.

In some embodiments, the operator can activate the unlock button 322 on the handle such as by depressing the unlock button 322. In some embodiments, the operator can move the slider 324 in a distal direction to advance at least one guide tube away from the catheter body until the distal end of the at least one guide tube is in proximity to the inside wall of the vessel.

In some embodiments, the operator can re-activate the unlock button 322, such as by depressing the unlock button 222. In some embodiments, the operator can move the slider 324 to extend the at least one wire 20 beyond the distal end of at least one guide tube 30. In some embodiments, the slider 224 will cause the at least one injector tube to penetrate through the inside wall of the target vessel. In some embodiments, the slider 224 will place the electrode 25 of at least one wire 20 into a volume of tissue outside of the inside wall of the target vessel. In some embodiments, the operator can apply energy to the electrode to ablate tissue. In some embodiments, the operator can apply energy to the electrode to sense nerves. In some embodiments, the operator can apply energy to the electrode to stimulate tissue.

Various other modifications, adaptations, and alternative designs are of course possible in light of the above teachings. Therefore, it should be understood at this time that within the scope of the appended claims the invention may be practiced otherwise than as specifically described herein.

Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The foregoing description and examples has been set forth to illustrate the disclosure according to various embodiments and are not intended as being unduly limiting. The headings provided herein are for organizational purposes only and should not be used to limit embodiments. Each of the disclosed aspects and examples of the present disclosure may be considered individually or in combination with other aspects, examples, and variations of the disclosure. In addition, unless otherwise specified, none of the steps of the methods of the present disclosure are confined to any particular order of performance. References cited herein are incorporated by reference in their entirety. The description of an embodiment as "preferred" does not limit the use or scope of alternative embodiments.

While the methods and devices described herein may be susceptible to various modifications and alternative forms, specific examples thereof have been shown in the drawings and are herein described in detail. It should be understood, however, that the embodiments disclosed should cover modifications, equivalents, and alternatives falling within the spirit and scope of the various embodiments described herein and the appended claims.

Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some examples, acts or events can be performed concurrently, e.g., through multi-threaded processing, interrupt processing, or multiple processors or processor cores or on other parallel architectures, rather than sequentially.

The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed.

The various illustrative logical blocks, modules, processes, methods, and algorithms described in connection with the embodiments disclosed herein can be implemented as electronic hardware, computer software, or combinations of both. To clearly illustrate this interchangeability of hardware and software, various illustrative components, blocks, modules, operations, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Conditional language used herein, such as, among others, "can," "might," "may," "e.g.," and the like, unless specifically stated otherwise, or otherwise understood within the context as used, is generally intended to convey that some examples include, while other examples do not include, certain features, elements, and/or states. Thus, such conditional language is not generally intended to imply that features, elements, blocks, and/or states are in any way required for one or more examples or that one or more examples necessarily include logic for deciding, with or without author input or prompting, whether these features, elements and/or states are included or are to be performed in any particular embodiment.

The methods disclosed herein may include certain actions taken by a practitioner; however, the methods can also include any third-party instruction of those actions, either expressly or by implication. For example, actions such as "positioning an electrode" include "instructing positioning of an electrode."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 hour" includes "1 hour." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure. The phrase "at least one of" is intended to require at least one item from the subsequent listing, not one type of each item from each item in the subsequent listing. For example, "at least one of A, B, and C" can include A, B, C, A and B, A and C, B and C, or A, B, and C.

What is claimed is:

1. A catheter comprising:
a catheter body having a central axis extending in a longitudinal direction, a distal portion including at least two guide tubes, each guide tube having a distal end and a lumen, the at least two guide tubes moveable between a first position within the catheter body and a second position inclined laterally away from the catheter body, wherein the at least two guide tubes are configured to be positioned with the distal ends in proximity to an inside wall of a target vessel;
at least two penetrators configured to penetrate the inside wall of the target vessel, a portion of a first penetrator of the at least two penetrators located coaxially inside of a first lumen of a first guide tube of the at least two guide tubes, a portion of a second penetrator of the at least two penetrators located coaxially inside of a second lumen of a second guide tube of the at least two guide tubes, wherein the first and second penetrators are guided by the first and second guide tubes, respectively, to the inside wall of the target vessel along different trajectories formed by the lumens, and
a proximal handle adapted to advance and retract the at least two guide tubes and the at least two penetrators, the proximal handle comprising an unlock mechanism having a locked state and an unlocked state, the proximal handle also having a movement mechanism configured to allow the relative longitudinal movement of the at least two guide tubes with respect to the catheter body and the at least two penetrators with respect to the at least two guide tubes, the movement subject to the unlock mechanism being in the unlocked state, where the movement mechanism is a slide switch.

2. The catheter of claim 1, including three guide tubes and three penetrators.

3. The catheter of claim 1, where at least one penetrator of the at least two penetrators is hollow and includes fluid egress near the distal end of the at least one penetrator, and where the catheter includes an injection lumen in fluid communication with the fluid egress of the at least one penetrator.

4. The catheter of claim 1, where at least one penetrator of the at least two penetrators has a distal end that forms an electrode, the catheter body further including a wire that runs the length of the catheter to conduct electrical signals between the at least one electrode and a connector near the proximal end of the catheter, the connector adapted to connect the wire to external equipment.

5. The catheter of claim 4, where the external equipment includes electronic systems selected from the group consisting of:
a sensor configured to measure electrical signals,
a sensor configured to measure electrical signals sensed by the electrode of the at least one penetrator of the at least two penetrators,
a signal generator configured to provide electrical stimulation signals to the electrode of the at least one penetrator, and
an energy delivery effector configured to provide energy based ablation through the electrode of the at least one penetrator.

6. The catheter of claim 1, where the proximal handle includes at least one marker line associated with a position of the movement mechanism denoting the catheter state selected from the group consisting of:
the position of the movement mechanism where the at least two guide tubes and at least two penetrators are both retracted,
the position of the movement mechanism where the at least two guide tubes are advanced but the at least two penetrators are retracted, and
the position of the movement mechanism where the at least two guide tubes and at least two penetrators are both advanced.

7. The catheter of claim 6, where two or more marker lines are included on the proximal handle.

8. The catheter of claim 6, where the proximal handle includes a first marker line denoting the position of the movement mechanism where the at least two guide tubes and at least two penetrators are both retracted, a second marker line denoting the position of the movement mechanism where the at least two guide tubes are advanced but the at least two penetrators are retracted, and a third marker line denoting the position of the movement mechanism where the at least two guide tubes and at least two penetrators are both advanced.

9. The catheter of claim 1, where the proximal handle includes at least one icon associated with the state of the catheter selected from the group consisting of:
the position of the movement mechanism where the at least two guide tubes and at least two penetrators are both retracted,
the position of the movement mechanism where the at least two guide tubes are advanced but the at least one penetrators are retracted, and
the position of the movement mechanism where the at least two guide tubes and at least two penetrators are both advanced.

10. The catheter of claim 9, where the proximal handle includes a first icon denoting the position of the movement mechanism where the at least two guide tubes and at least two penetrators are both retracted, a second icon denoting the position of the movement mechanism where the at least two guide tubes are advanced but the at least two penetrators are retracted, and a third icon denoting the position of the movement mechanism where the at least two guide tubes and at least two injector tubes are both advanced.

11. The catheter of claim 9, where the proximal handle includes two of each of the three icons.

12. The catheter of claim 1, where the handle includes at least one flushing port.

13. The catheter of claim 1, where the handle includes a finger detent to aid in positioning an operator's hand for operating the handle.

14. The catheter of claim 6, where there is at least one marker line on the top surface of the handle.

15. The catheter of claim 14, where there are at least two marker lines on the top surface of the handle.

16. The catheter of claim 9, where the at least one icon is placed in a location selected from the group consisting of:
the top surface of the handle,
one of the side surfaces of the handle,
both side surfaces of the handle, and
a chamfer or filleted surface between the top surface and a side surface of the handle.

17. The catheter of claim 1, wherein the at least two guide tubes are configured to be positioned with the distal ends in proximity to the inside wall of the target vessel to define separate trajectories to the target vessel, wherein a portion of the at least two penetrators are configured to slide relative to the at least two guide tubes along the separate trajectories into the target vessel.

18. The catheter of claim 1, wherein the at least two guide tubes are configured to be positioned with the distal ends in proximity to the inside wall of the target vessel at different circumferential locations in the second position, wherein the at least two penetrators are configured to circumferentially penetrate the inside wall of a target vessel guided by the at least two guide tubes.

* * * * *